(12) United States Patent
Einav et al.

(10) Patent No.: US 10,978,193 B2
(45) Date of Patent: Apr. 13, 2021

(54) SYSTEM AND METHOD OF PHARMACEUTICAL OPERATIONS FOR POST-ACUTE CARE FACILITIES LONG-TERM CARE FACILITIES

(71) Applicant: Tech Pharmacy Services, LLC, Fort Lee, NJ (US)

(72) Inventors: Omer Einav, Kfar-Monash (IL); Doron Shabanov, Tzur-Yigal (IL); Yoav Kestel, Ramat-HaSharon (IL); Yuval Siman, Givatayim (IL); Tamir Ben David, Tel-Aviv (IL); Eyal Lifschitz, Givat Shmuel (IL); Anthony Joseph Spero, Queensbury, NY (US); Thomas A. McKinney, Boonton, NJ (US)

(73) Assignee: Tech Pharmacy Services, LLC, Fort Lee, NJ (US)

( * ) Notice: Subject to any disclaimer, the term of this patent is extended or adjusted under 35 U.S.C. 154(b) by 0 days.

(21) Appl. No.: 16/214,081

(22) Filed: Dec. 9, 2018

(65) Prior Publication Data
US 2020/0185076 A1    Jun. 11, 2020

(51) Int. Cl.
*G16H 20/13*    (2018.01)
*G16H 40/67*    (2018.01)
*G16H 40/20*    (2018.01)

(52) U.S. Cl.
CPC ............. *G16H 20/13* (2018.01); *G16H 40/20* (2018.01); *G16H 40/67* (2018.01)

(58) Field of Classification Search
CPC ............................. G06Q 10/087; G16H 50/80
See application file for complete search history.

(56) References Cited

U.S. PATENT DOCUMENTS

| | | |
|---|---|---|
| 5,405,048 A | 4/1995 | Rogers et al. |
| RE35,743 E | 3/1998 | Pearson |
| 6,006,946 A | 12/1999 | Williams et al. |
| 6,529,801 B1 | 3/2003 | Rosenblum |
| 7,698,019 B2 | 4/2010 | Moncrief et al. |
| 8,027,849 B2 | 9/2011 | Johnson et al. |

(Continued)

FOREIGN PATENT DOCUMENTS

| | | |
|---|---|---|
| WO | WO 2004/036481 | 4/2004 |
| WO | WO 2005/043440 | 5/2005 |

(Continued)

OTHER PUBLICATIONS

Official Action dated Aug. 5, 2019 From the US Patent and Trademark Office Re. U.S. Appl. No. 16/379,831. (25 pages).

(Continued)

*Primary Examiner* — Reginald R Reyes

(57) ABSTRACT

According to an aspect of some embodiments of the present invention there is provided a system of pharmaceutical dispensing for at least one first facility, comprising: a data processing and management computer; a facility pharmacy management software; a communications network in communication with said facility pharmacy group management server; at least one pharmaceutical storage and electronic dispensing machine; said system further comprises at least one supplemental supplier of said plurality of pharmaceuticals in case said at least one pharmaceutical storage and electronic dispensing machine cannot dispense.

23 Claims, 25 Drawing Sheets

(56) References Cited

U.S. PATENT DOCUMENTS

| | | |
|---|---|---|
| 8,219,243 B2 | 7/2012 | Haas |
| 8,280,550 B2 | 10/2012 | Levy et al. |
| 8,521,327 B2 | 8/2013 | Pinney et al. |
| 8,991,138 B2 | 3/2015 | Yuyama et al. |
| 9,031,690 B2 | 5/2015 | Cotner |
| 9,779,215 B2 | 10/2017 | Rosenblum |
| 9,908,704 B2 | 3/2018 | Hawkes et al. |
| 10,007,764 B2 | 6/2018 | Kim |
| 10,049,188 B2 | 8/2018 | Iantorno et al. |
| 10,614,916 B1 | 4/2020 | Einav et al. |
| 2003/0024943 A1 | 2/2003 | MacDonald |
| 2004/0155049 A1 | 8/2004 | Float et al. |
| 2005/0259818 A1* | 11/2005 | Silverbrook ........... G06Q 40/08 380/55 |
| 2009/0321469 A1 | 12/2009 | Knoth |
| 2011/0017764 A1 | 1/2011 | Liguori et al. |
| 2011/0315588 A1 | 12/2011 | Ross et al. |
| 2012/0004770 A1 | 1/2012 | Ooyen et al. |
| 2012/0209619 A1* | 8/2012 | Knotts .................. G16H 20/13 705/2 |
| 2013/0123977 A1 | 5/2013 | Sanders et al. |
| 2013/0240555 A1 | 9/2013 | Kim |
| 2014/0262690 A1 | 9/2014 | Henderson et al. |
| 2015/0081326 A1 | 3/2015 | Krishnapuram et al. |
| 2015/0154709 A1 | 6/2015 | Cook |
| 2016/0068328 A1 | 3/2016 | Lam et al. |
| 2016/0132404 A1 | 5/2016 | Munson et al. |
| 2017/0132867 A1 | 5/2017 | Berg et al. |
| 2017/0267453 A1 | 9/2017 | Hellenbrand |
| 2018/0122177 A1 | 5/2018 | Este et al. |
| 2018/0357596 A1* | 12/2018 | Bedford ............... G06Q 10/087 |
| 2020/0323737 A1 | 10/2020 | Einav et al. |
| 2020/0327980 A1 | 10/2020 | Einav et al. |
| 2020/0388369 A1 | 12/2020 | Einav et al. |

FOREIGN PATENT DOCUMENTS

| | | |
|---|---|---|
| WO | WO 2018/052160 | 3/2018 |
| WO | WO 2020/121165 | 6/2020 |
| WO | WO 2020/208439 | 10/2020 |
| WO | WO 2020/208477 | 10/2020 |
| WO | WO 2020/208479 | 10/2020 |

OTHER PUBLICATIONS

Official Action dated May 15, 2019 From the US Patent and Trademark Office Re. U.S. Appl. No. 16/379,831. (24 pages).

Applicant-Initiated Interview Summary dated Jul. 12, 2019 From the US Patent and Trademark Office Re. U.S. Appl. No. 16/379,831. (3 pages).

International Search Report and the Written Opinion dated Mar. 22, 2020 From the International Searching Authority Re. Application No. PCT/IB2019/060572. (14 Pages).

International Search Report and the Written Opinion dated Jun. 25, 2020 From the International Searching Authority Re. Application No. PCT/IB2020/052052. (10 Pages).

International Search Report and the Written Opinion dated Jun. 25, 2020 From the International Searching Authority Re. Application No. PCT/IB2020/053080. (13 Pages).

International Search Report and the Written Opinion dated Jun. 28, 2020 From the International Searching Authority Re. Application No. PCT/IB2020/053082. (13 Pages).

Interview Summary dated Jul. 21, 2020 from the US Patent and Trademark Office. Re. U.S. Appl. No. 16/430,456. (3 pages).

Official Action dated Jul. 17, 2020 from the US Patent and Trademark Office Re. U.S. Appl. No. 16/559,716. (17 pages).

Official Action dated Jun. 25, 2020 from the US Patent and Trademark Office Re. U.S. Appl. No. 16/430,456. (15 pages).

Restriction Official Action dated Jul. 24, 2020 from the US Patent and Trademark Office Re. U.S. Appl. No. 16/379,835. (6 pages).

International Search Report and the Written Opinion dated Aug. 31, 2020 From the International Searching Authority Re. Application No. PCT/IB2020/055232.

Interview Summary dated Jan. 8, 2021 from the US Patent and Trademark Office Re. U.S. Appl. No. 16/379,835. (4 pages).

* cited by examiner

SYSTEM AND METHOD OF PHARMACEUTICAL OPERATIONS FOR POST-ACUTE CARE FACILITIES LONG-TERM CARE FACILITIES

FIELD AND BACKGROUND OF THE INVENTION

The present invention, in some embodiments thereof, relates to nursing home, retirement home, assisted living facility, and other long-term care industries in general and, more particularly, to pharmaceutical dispensing operations for such long-term care facilities.

Additional background art includes U.S. Pat. No. 7,698, 019 which discloses "a system, software and related methods of enhanced pharmaceutical operations in long term care facilities are provided. An embodiment of a system includes a long-term care facility pharmacy group management server, long-term care facility pharmacy management software associated with the long-term care facility pharmacy group management server to manage pharmacological operations in a plurality of long-term care facilities, a plurality of pharmaceutical storage and electronic dispensing carts each positioned in a long-term care facility remote from the long-term care facility pharmacy group management server and in communication therewith, a remote pharmacy group server in communication with the long-term care facility pharmacy group management server, and a plurality of pharmaceutical prescription document processors each positioned in a long-term care facility and in communication with the remote pharmacy group server or the long-term care facility pharmacy group management server".

SUMMARY OF THE INVENTION

According to an aspect of some embodiments of the present invention there is provided a method of providing a pharmaceutical dispensing service to at least one facility, comprising: providing at least one first pharmaceutical storage and dispensing machine to said at least one first facility; said at least one first pharmaceutical storage and dispensing machine in communication with at least one facility pharmacy management server; providing a pharmacy group management computer being positioned remote from said at least one first facility to manage and control said at least one first pharmaceutical storage and dispensing machine defining a facility pharmacy management server; providing at least one supplemental supplier of pharmaceuticals; wherein said method further comprises selecting said at least one supplemental supplier of pharmaceuticals so as to ensure dispensing of pharmaceuticals to users according to a predetermined schedule.

According to some embodiments of the invention, the method further comprises providing at least one second pharmaceutical storage and dispensing machine as supplemental supplier of pharmaceuticals.

According to some embodiments of the invention, said providing at least one second pharmaceutical storage and dispensing machine further comprises allocating said at least one second pharmaceutical storage and dispensing machine at the same facility as said at least one first pharmaceutical storage and dispensing machine.

According to some embodiments of the invention, said providing at least one second pharmaceutical storage and dispensing machine further comprises allocating said at least one second pharmaceutical storage and dispensing machine at a second facility; said second facility located in the vicinity of said first facility.

According to some embodiments of the invention, said providing at least one second pharmaceutical storage and dispensing machine further comprises allocating said at least one second pharmaceutical storage and dispensing machine at a third facility; said third facility located far from said first facility.

According to some embodiments of the invention, the method further comprises providing communication with at least one pharmacy as supplemental supplier of pharmaceuticals.

According to some embodiments of the invention, said pharmacy comprises a pharmaceutical storage and dispensing machine.

According to some embodiments of the invention, the method further comprises providing communication with at least one storage unit as supplemental supplier of pharmaceuticals.

According to some embodiments of the invention, information regarding said predetermined schedule is located in said pharmacy group management computer.

According to an aspect of some embodiments of the present invention there is provided a system of pharmaceutical dispensing for at least one first facility, comprising: a data processing and management computer including a first memory to store data therein to manage and control at least one pharmaceutical storage and dispensing machine positioned remote therefrom and to thereby define a facility pharmacy group management server; a facility pharmacy management software stored in said first memory of said facility pharmacy group management server to manage pharmaceutical operations in said at least one facility, to process distribution of pharmaceuticals stored in said at least one pharmaceutical storage and dispensing machine during preselected dispensing time periods; a communications network in communication with said facility pharmacy group management server; at least one pharmaceutical storage and dispensing machine positioned in said at least one facility remote from said facility pharmacy group management server, in communication with said facility pharmacy group management server through said communication network, to store a plurality of pharmaceuticals therein, and to individually retrieve at least one pharmaceutical of said plurality of pharmaceuticals stored in said pharmaceutical storage and dispensing machine, load said at least one pharmaceutical of the plurality of pharmaceuticals into one of a plurality of disposable individual patient dosing packages, package said at least one pharmaceutical, and dispense said loaded and packaged one of said plurality of individual patient dosing packages into a separate and removable container associated with said machine for use by authorized personnel located at said facility; wherein said system further comprises at least one supplemental supplier of said plurality of pharmaceuticals adapted to dispense said pharmaceuticals to the users at said preselected dispensing time periods.

According to some embodiments of the invention, said at least one supplemental supplier is a second pharmaceutical storage and dispensing machine located at the same facility.

According to some embodiments of the invention, said at least one supplemental supplier is a second pharmaceutical storage and dispensing machine located at a second facility; said second facility located near said facility.

According to some embodiments of the invention, said at least one supplemental supplier is a second pharmaceutical storage and dispensing machine located at a second facility; said second facility located far from said facility.

According to some embodiments of the invention, said at least one supplemental supplier is a pharmacy located near said facility.

According to some embodiments of the invention, said at least one supplemental supplier is a storage unit.

According to an aspect of some embodiments of the present invention there is provided a method of storage organization in a pharmaceutical dispensing system, comprising: providing a plurality of storage units in communication with a server of said pharmaceutical dispensing system; collecting pharmaceutical dispensing information of facilities receiving pharmaceuticals from said pharmaceutical dispensing system; collecting information regarding said pharmaceuticals; providing at least one parameter for analysis; analyzing collected information using said at least one parameter; distributing pharmaceuticals between said plurality of storage units according to the result of said analysis.

According to some embodiments of the invention, said at least one parameter is commonly used pharmaceuticals that are not yet prescribed to specific tenants but likely to be required.

According to some embodiments of the invention, said at least one parameter is predicted pharmaceuticals that are not yet prescribed to specific tenants but likely to be required.

According to some embodiments of the invention, a scale of importance is added to said at least one parameter by a system supervisor to enable prioritizing of parameters.

According to some embodiments of the invention, said at least one parameter is at least one selected from the group consisting of: required pharmaceuticals for a current population in said facilities; common prescribed pharmaceuticals; pharmaceuticals dispensed on a regular basis; life expectancy of said pharmaceuticals; a location of use of said pharmaceuticals; frequency of use of said pharmaceuticals; type of said pharmaceuticals; cost of said pharmaceuticals; any combination thereof.

According to some embodiments of the invention, said at least one parameter is required pharmaceuticals for a current population in said facilities.

According to some embodiments of the invention, said at least one parameter is common prescribed pharmaceuticals.

According to some embodiments of the invention, said at least one parameter is pharmaceuticals dispensed on a regular basis.

According to some embodiments of the invention, said at least one parameter is life expectancy of said pharmaceuticals.

According to some embodiments of the invention, said at least one parameter is a location of use of said pharmaceuticals.

According to some embodiments of the invention, said at least one parameter is frequency of use of said pharmaceuticals.

According to some embodiments of the invention, said at least one parameter is type of said pharmaceuticals.

According to some embodiments of the invention, said at least one parameter is cost of said pharmaceuticals.

According to some embodiments of the invention, said at least one parameter is level of automation of a storage facility.

According to some embodiments of the invention, said at least one parameter is distance between said storage units and said facilities.

According to some embodiments of the invention, said pharmaceutical dispensing information is life expectancy of said pharmaceuticals.

According to some embodiments of the invention, said pharmaceutical dispensing information is cost of said pharmaceuticals.

According to some embodiments of the invention, said pharmaceutical dispensing information is expected time of supply from the pharmaceuticals suppliers.

According to some embodiments of the invention, said pharmaceutical dispensing information is type of said pharmaceuticals.

According to some embodiments of the invention, said pharmaceutical dispensing information is form that said pharmaceutical is provided.

According to some embodiments of the invention, said pharmaceutical dispensing information is security requirements for said pharmaceuticals.

According to some embodiments of the invention, said pharmaceutical information is at least one selected from the group consisting of: life expectancy of said pharmaceuticals; cost of said pharmaceuticals; expected time of supply from the pharmaceuticals suppliers; type of said pharmaceuticals; form that said pharmaceutical is provided; security requirements for said pharmaceuticals; any combination thereof.

According to some embodiments of the invention, said pharmaceutical information is life expectancy of said pharmaceuticals.

According to some embodiments of the invention, said pharmaceutical information is cost of said pharmaceuticals.

According to some embodiments of the invention, said pharmaceutical information is expected time of supply from the pharmaceuticals suppliers.

According to some embodiments of the invention, said pharmaceutical information is type of said pharmaceuticals.

According to some embodiments of the invention, said pharmaceutical information is form that said pharmaceutical is provided.

According to some embodiments of the invention, said pharmaceutical information is security requirements for said pharmaceuticals.

According to an aspect of some embodiments of the present invention there is provided a method of tracking users to dispense pharmaceuticals to said users in a pharmaceutical dispensing system, comprising: providing at least one expected location of a user in a facility at at least one time; assessing if said user is at said at least one expected location in said facility at said at least one time; if said user is at said at least one expected location in said facility at said at least one time, then dispense pharmaceuticals; if said user is not at said at least one expected location in said facility at said at least one time, then: assessing if said user is at a different location within said facility at said at least one time; if said user is at a different location within said facility at said at least one time, then update said different location and dispense pharmaceuticals at said different location; if said user is not at a different location within said facility at said at least one time, then: assessing if said user is at a different facility at said at least one time; if said user is at a different facility at said at least one time, then update location to said different facility location and dispense pharmaceuticals at said different facility location; if said user is not at a different facility at said at least one time, then: assessing if said user is at different address but not in a facility; if said user is at a different address not within a facility at said at least one time, then update said different address location and dispense pharmaceuticals at said different address location; if said user is not at a different address location not within a facility at said at least one time, then: evaluating user status.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic representation of an exemplary prior art system;

FIGS. 2a-b are schematic representations of an exemplary basic pharmaceutical dispensing system, according to some embodiments of the invention;

Figure 8A:
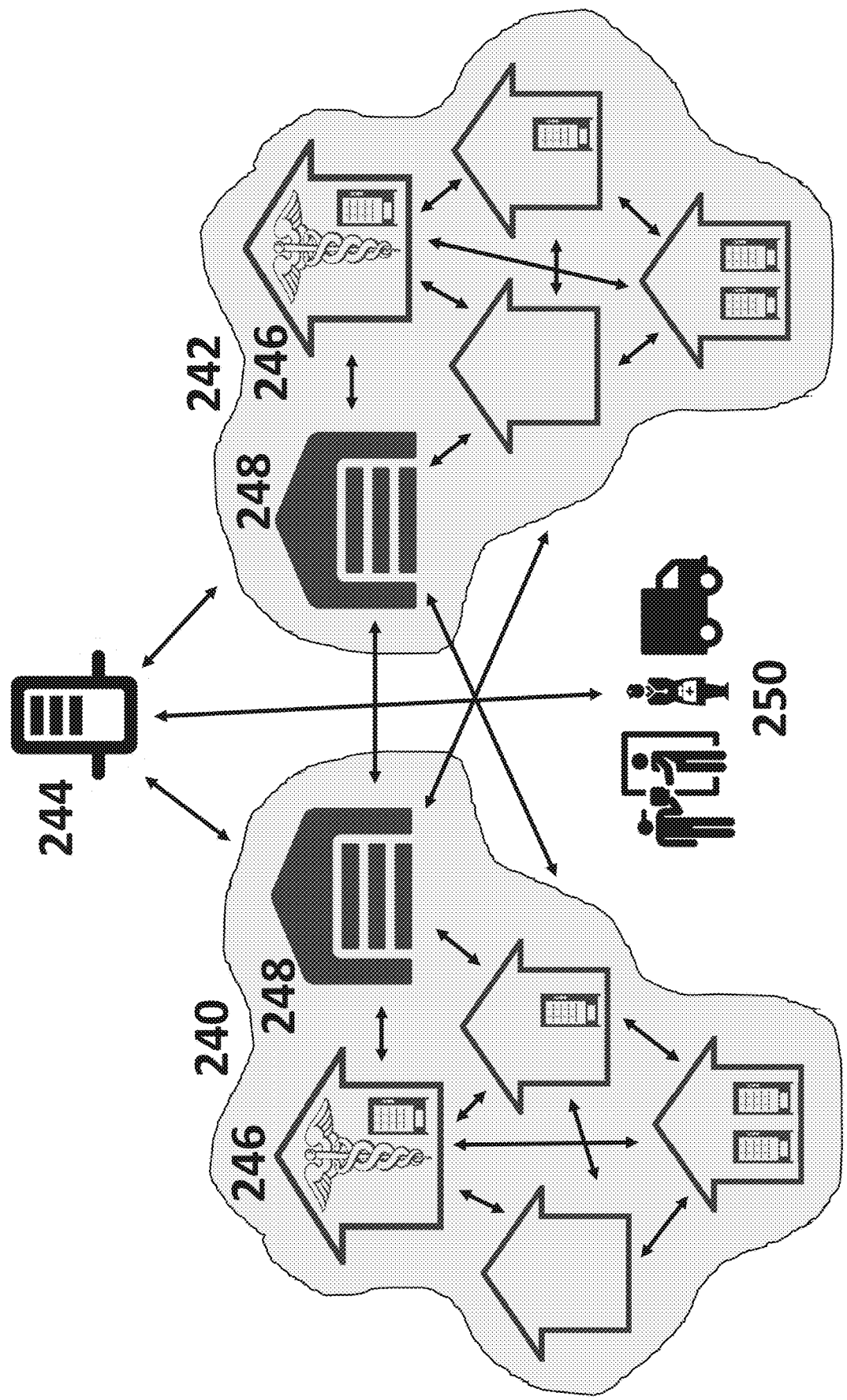
Figure 8B:
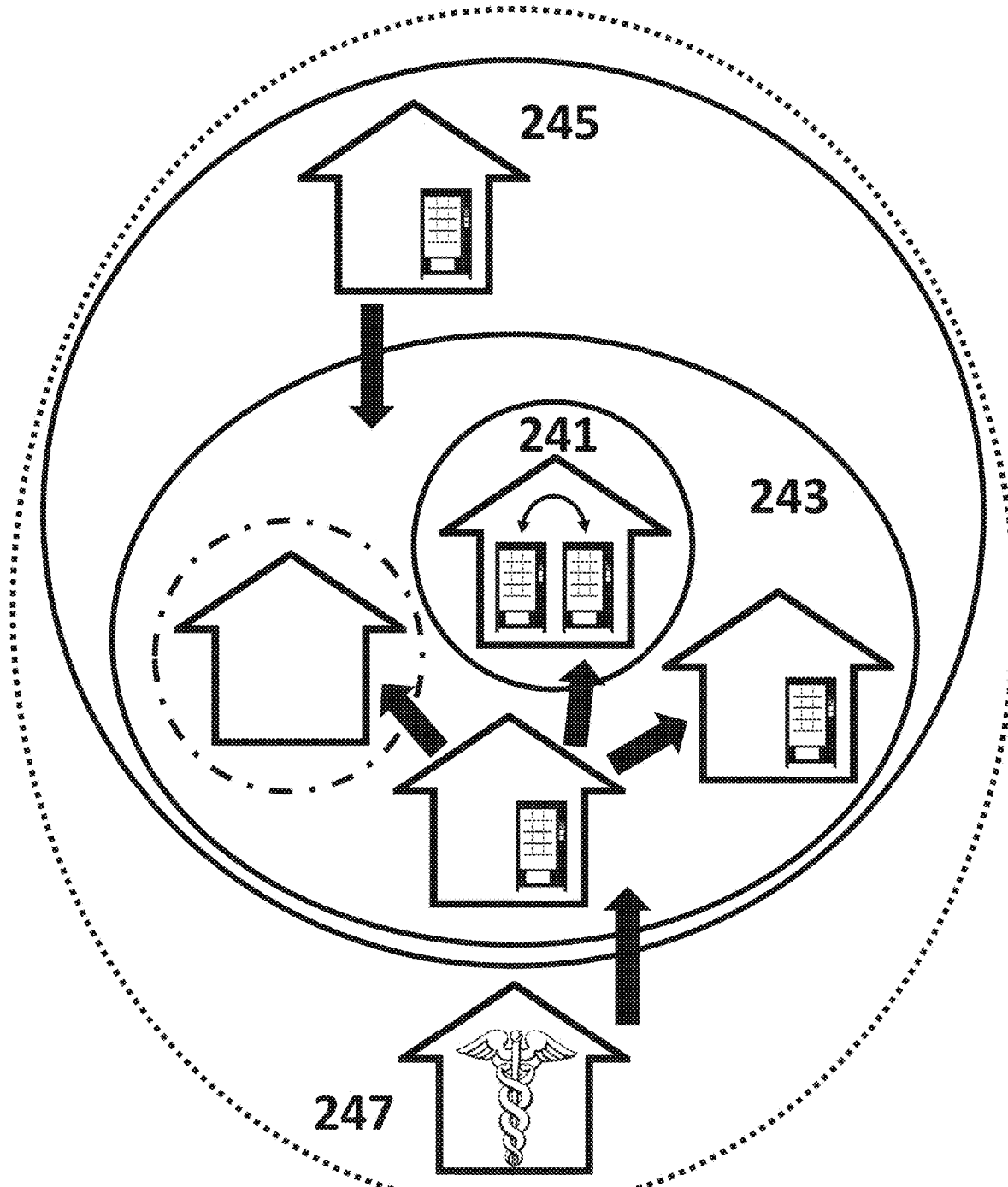
Figure 21:
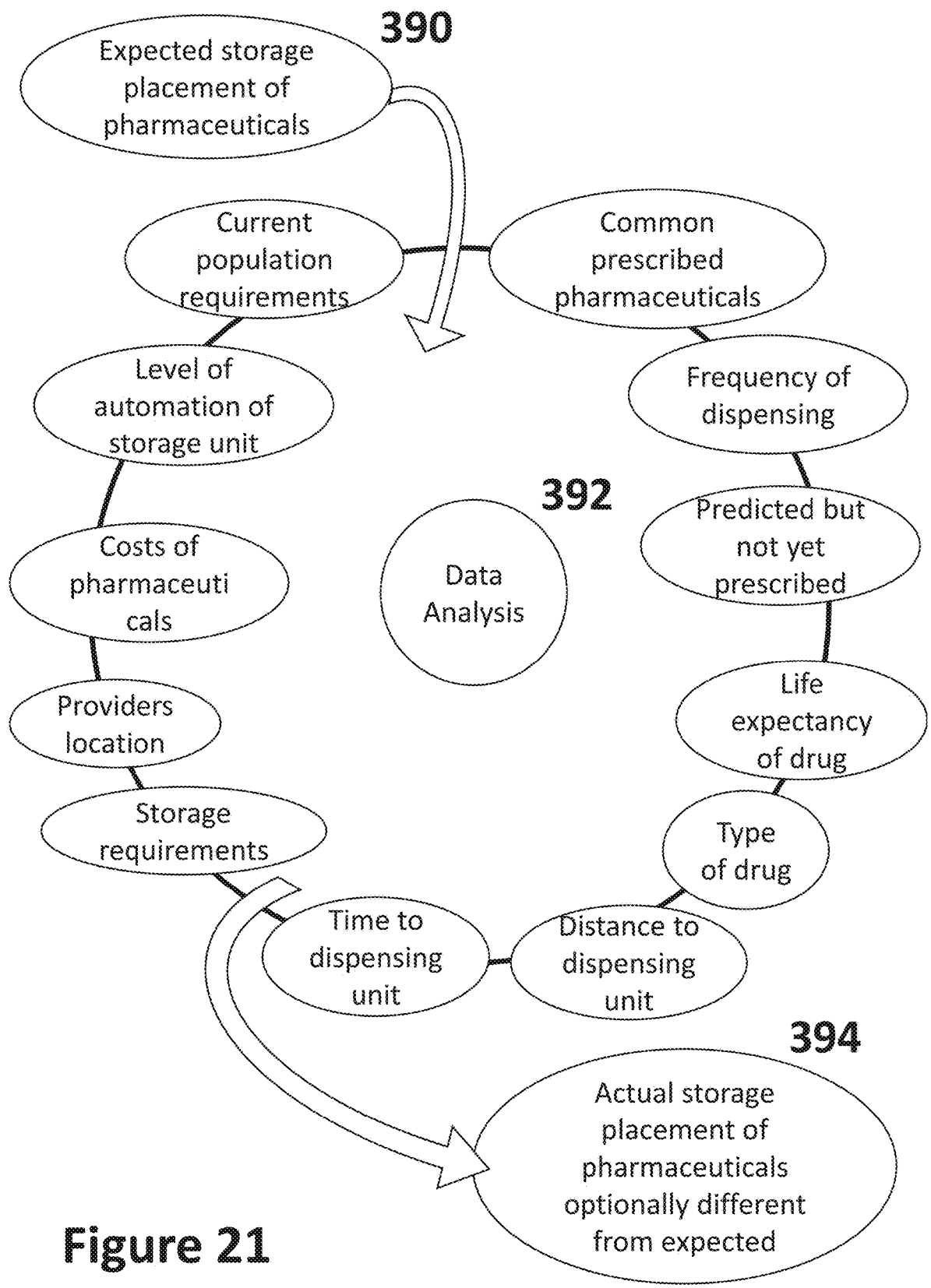
Figure 22:
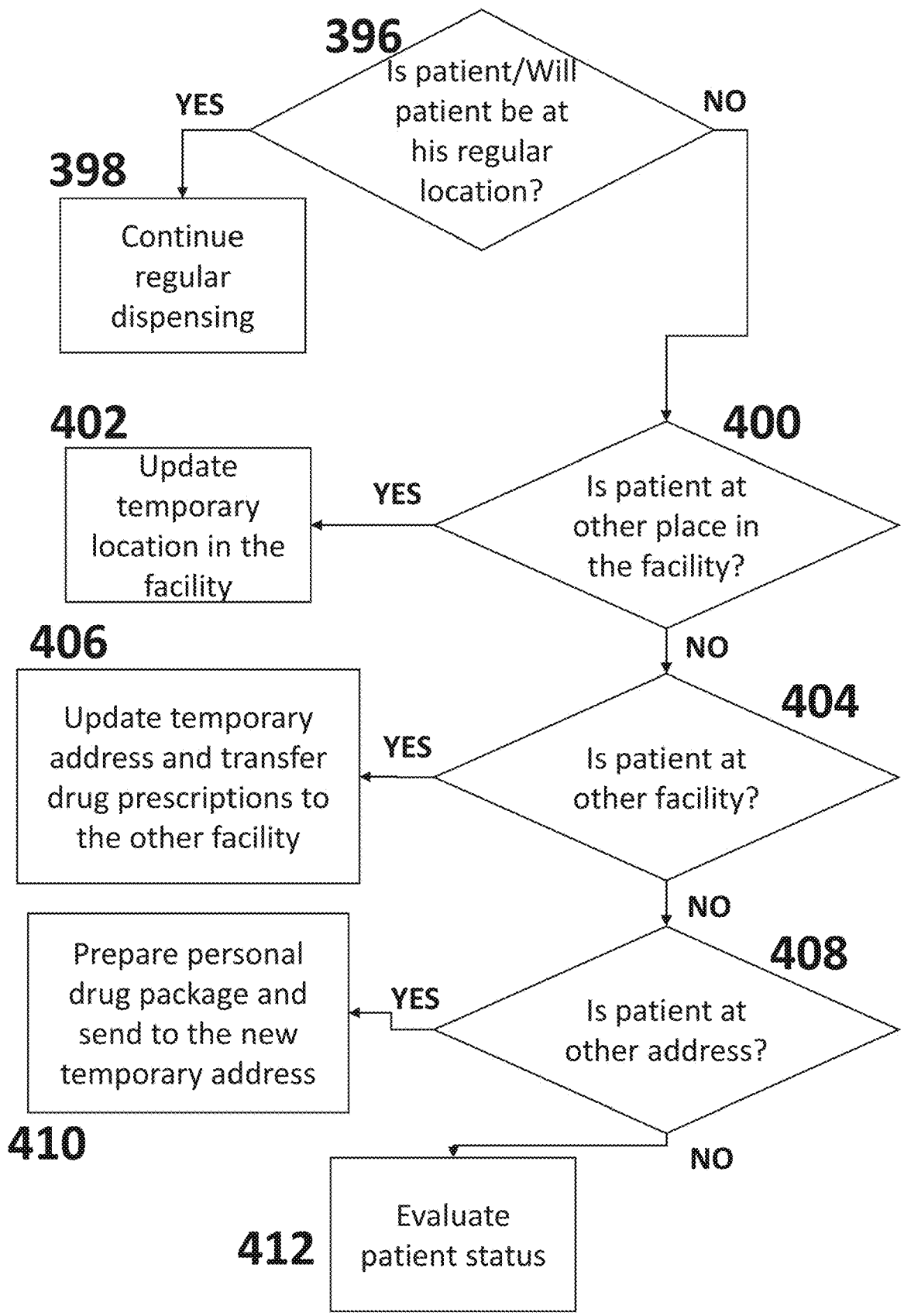
Figure 23:
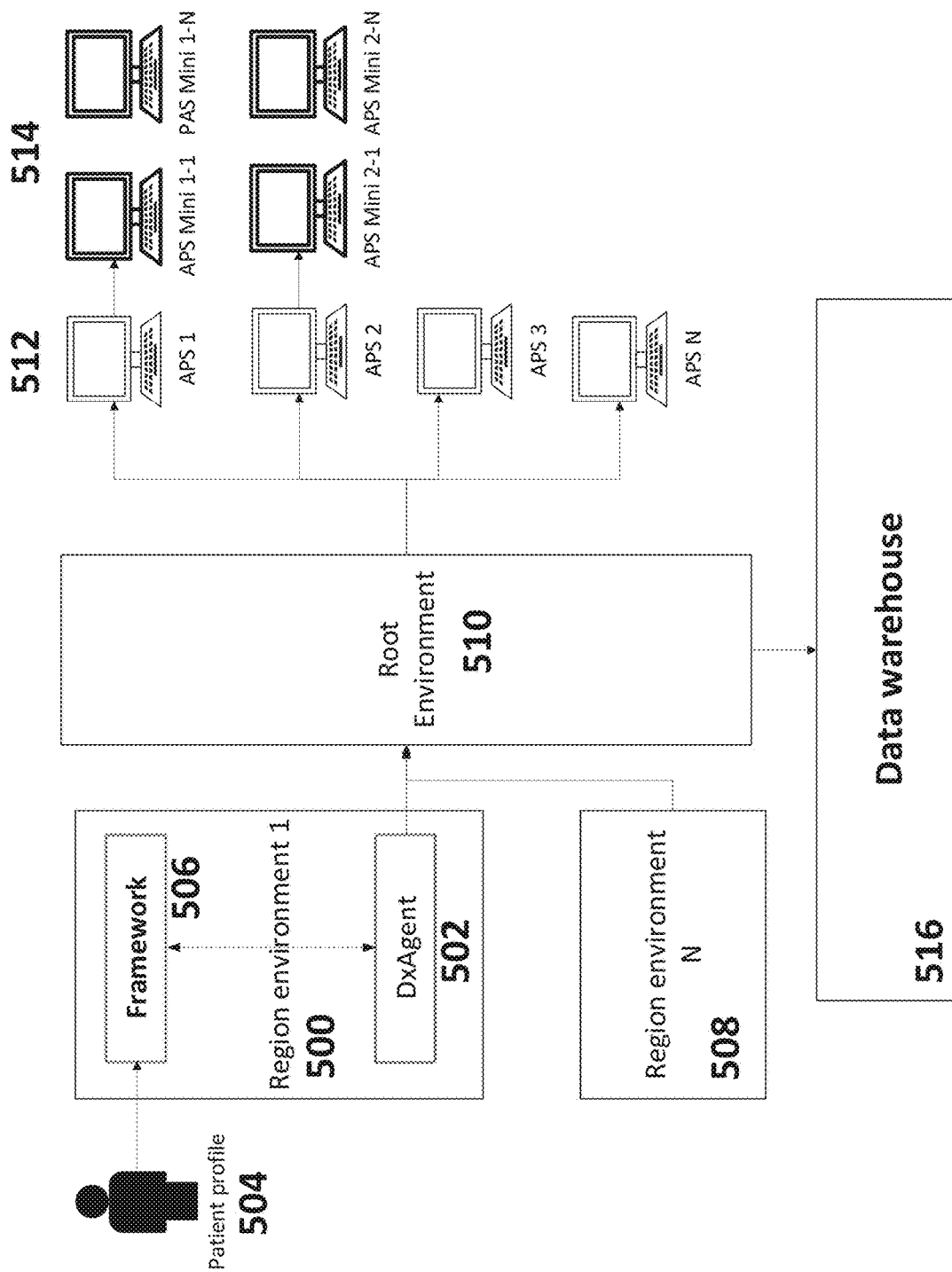

FIGS. 8a-b are schematic representations of the possible interactions in a pharmaceutical dispensing ecosystem, according to some embodiments of the invention;

FIGS. 9-12 are schematic flowcharts of a method of management and operations performed by an exemplary pharmaceutical dispensing system, according to some embodiments of the invention;

FIGS. 13-20 are schematic flowcharts of a method of management and operations performed by an exemplary server of the pharmaceutical dispensing system, according to some embodiments of the invention;

FIG. 21 is a schematic representation of a methodology of organizing the storage of pharmaceuticals in a pharmaceutical dispensing system;

FIG. 22 is a schematic flowchart of a tracking method performed by an exemplary pharmaceutical dispensing system, according to some embodiments of the invention, and FIG. 23 is a schematic representation of the connection and/or interface between the electronic medical record of the facility and the plurality of management softwares, according to some embodiments of the represent invention.

DESCRIPTION OF SPECIFIC EMBODIMENTS OF THE INVENTION

The present invention, in some embodiments thereof, relates to Long Term Acute Care Hospitals, Skilled Nursing, nursing home, retirement home, assisted living facility, and other long-term care industries in general and, more particularly, to pharmaceutical operations within nursing homes, retirement homes, assisted living facilities, and other long-term care facilities; also to pharmaceutical operations between nursing homes, retirement homes, assisted living facilities and other long-term care facilities, and a pharmaceutical dispensing system.

Overview

A broad aspect of some embodiments of the invention relates to means and methods of operation in a pharmaceutical dispensing system. In some embodiments, the system comprises units, personnel and users, for example, long-term care facilities, the personnel working at the long-term care facilities, pharmacies, drug-dispensing units, logistic units and the users. In some embodiments, the pharmaceutical dispensing system is global (i.e. the whole world). In some embodiments, the pharmaceutical dispensing system is a defined as a plurality of sub pharmaceutical dispensing systems working in coordination. In some embodiments, each of the sub pharmaceutical dispensing systems is responsible for a specific zone, for example, a country and/or a state and/or a city; and/or responsible for a specific role, for example, distribution and/or storage and/or maintenance and/or support. In some embodiments, a sub pharmaceutical dispensing system interacts with at least one other sub pharmaceutical dispensing system.

A broad aspect of the present invention relates to providing a patient with a pharmaceutical by providing a plurality of dispensing options and selecting at least one dispensing option from said plurality of dispensing options, in a pharmaceutical dispensing system.

An aspect of some embodiments of the invention relates to support for pharmaceutical dispensing units of a pharmaceutical dispensing system located in long-term care facilities. In some embodiments, a drug-dispensing unit receives support from another drug-dispensing unit within the same long-term care facility. In some embodiments, a drug-dispensing unit located in a long-term care facility receives support from another drug-dispensing unit located in a different long-term care facility. In some embodiments, a drug-dispensing unit located in a long-term care facility receives support from a pharmaceutical storage unit. In some embodiments, a drug-dispensing unit located in a long-term care facility receives support from a pharmacy. Optionally, the pharmacy comprises a drug-dispensing unit. In some embodiments, the pharmaceutical dispensing system coordinates the support to and between all long-term care facilities.

An aspect of some embodiments of the invention relates to providing a pharmaceutical dispensing service to a location (e.g. long-term care facility) that do not comprises a drug-dispensing unit. In some embodiments, a location that do not comprises a drug-dispensing units means a location that do not comprises a physical machine related to the system. Optionally, a location that do not comprises a drug-dispensing units means a location that requires additional transportation from the place of packaging to the final destination of dispensing. In some embodiments, a pharmaceutical dispensing service means receiving pharmaceuticals from a drug-dispensing machine. In some embodiments, said parameters are time and/or distance from the closest drug dispensing unit. In some embodiments, a drug-dispensing unit located in a long-term care facility provides a pharmaceutical dispensing service to the facility that do not comprises a drug-dispensing unit. In some embodiments, a pharmaceutical storage unit provides a pharmaceutical dispensing service to the facility that do not comprises a drug-dispensing unit. In some embodiments, a pharmacy provides a pharmaceutical dispensing service to the facility that do not comprises a drug-dispensing unit. Optionally, the pharmacy comprises a drug-dispensing unit.

An aspect of some embodiments of the invention relates to pharmaceutical tracking dispensing system for users in long-term care facilities in a pharmaceutical dispensing system. In some embodiments, the tracking system uses a personalized schedule of each user in a long-term care facility. In some embodiments, the personalized schedule includes information regarding drug-dispensing schedule and type of drug. In some embodiments, the personalized schedule includes information regarding the physical location of the user. In some embodiments, the tracking system uses the personal electronic devices of the user (i.e. cellphone, tablet, smartwatch). In some embodiments, the dispensing of the drug is coordinated with the location of the user. In some embodiments, the dispensing of the drug comprises choosing a facility that can provide the drug that is the closest to the location of the user.

An aspect of some embodiments of the invention relates to organization of the dispensing of pharmaceuticals to pharmaceutical dispensing units and/or users in long-term care facilities. In some embodiments, the system collects and analyzes information regarding the drug-dispensing behavior of long-term care facilities. In some embodiments, drug-dispensing behavior includes types of pharmaceuticals and/or quantity of pharmaceuticals and/or frequency of dispensing of pharmaceuticals. In some embodiments, the system organizes the geographical allocation of pharmaceuticals in pharmaceutical storage units according to parameters recovered from the analysis of the drug-dispensing behavior. In some embodiments, the system allocates and/or re-allocates pharmaceuticals according to predictive algorithms using parameters derived from drug-dispensing behavior analysis. In the past, storage of pharmaceuticals was directly decided by the actual location of the users, for example, a long term facility would store the required pharmaceuticals in-house since the users are located in the long term facility. Therefore, it was expected that the storage of pharmaceuticals would be, for example, on the same place as the users. In some embodiments, the actual storage location of the pharmaceuticals is different from the expected storage location of the pharmaceuticals. In some embodiments, the storage placement of the pharmaceuticals is not the same place as the users. In some embodiments, the actual storage placement of the pharmaceuticals is different from the expected storage placement. In some embodiments, the system comprises the information regarding an expected location for pharmaceutical storage. In some embodiments, the system may or may not require the information regarding an expected location for pharmaceutical storage for providing a storage placement for pharmaceuticals.

Before explaining at least one embodiment of the invention in detail, it is to be understood that the invention is not necessarily limited in its application to the details of construction and the arrangement of the components and/or units and/or methods set forth in the following description and/or illustrated in the drawings and/or the Examples. The invention is capable of other embodiments or of being practiced or carried out in various ways.

Prior Art

Over the years, pharmacies have been a backbone in providing prescription drugs and other medications to people and have been a convenience as retail pharmacies have expanded to locations close to most residential areas. Today the primary dispensing method in Long Term Care facilities is through dispensing at a long term care pharmacy. Packing the medication(s) in a traditional blister pack and or otherwise known as punch card and then delivered via a courier service to the facility where the patient resides. Recently, pharmacies also have been placed inside of facilities such as hospitals, physician offices, malls, nursing homes, retirement homes, assisted living facilities, and other locations to make it easier for people to get access to medications and to facilitate interaction with medical personnel.

Figure 1:
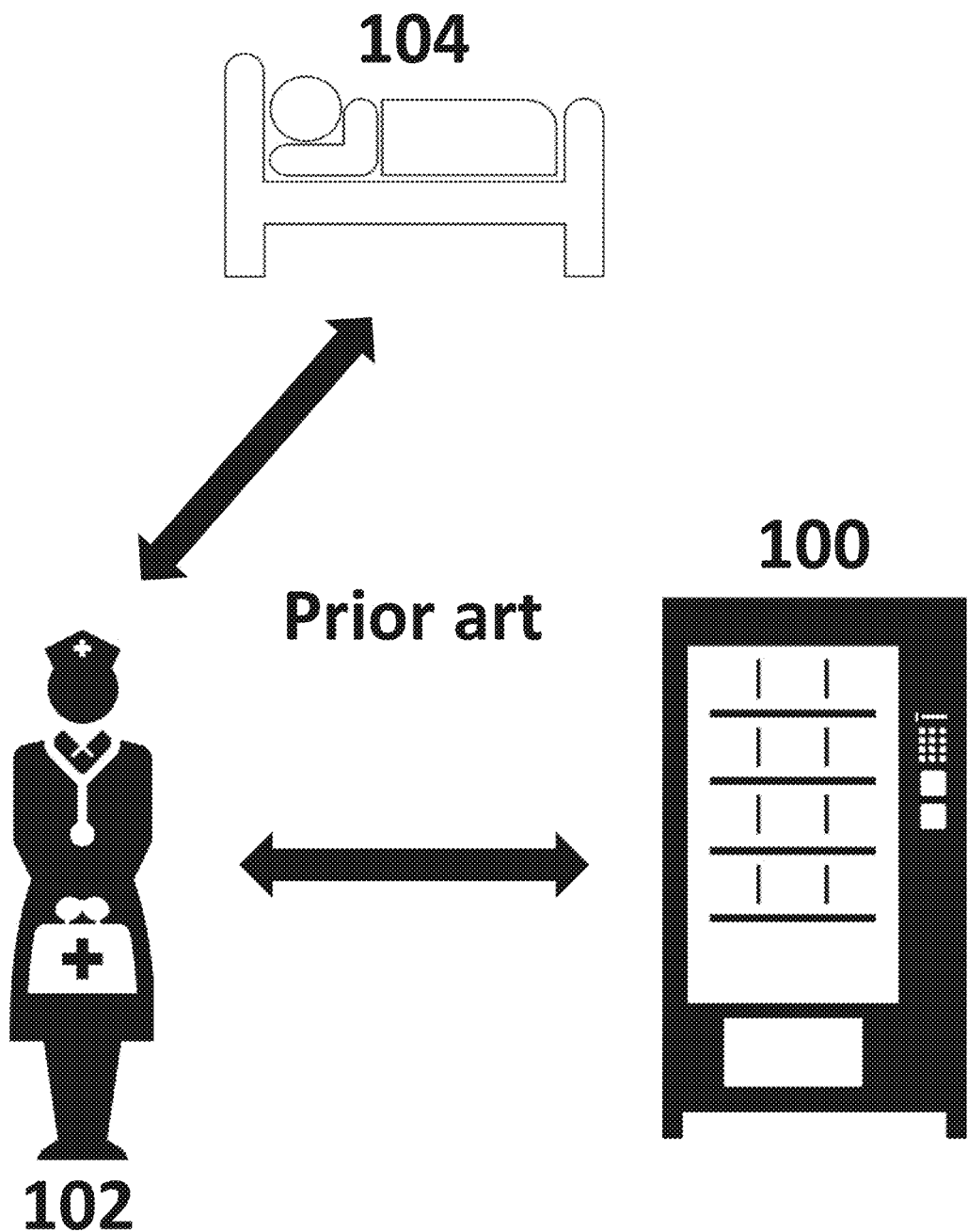

Referring now to FIG. 1, showing a schematic representation of an exemplary prior art system used, for example, in a long term care facility. The system comprises a storage and dispensing machine 100, which is brought to the long term care facility. There, a nurse 102 collects the pharmaceuticals and brings them to the patients 104.

It is common, in these prior art systems, that the machine stops working due to, for example, a technical malfunction, maintenance or unscheduled refill of pharmaceuticals. In any of these scenarios, the personnel of the long term care facility is required again to deal directly with the pharmaceuticals until the machine is repaired and/or resupplied.

Exemplary Basic system

Figure 2A:
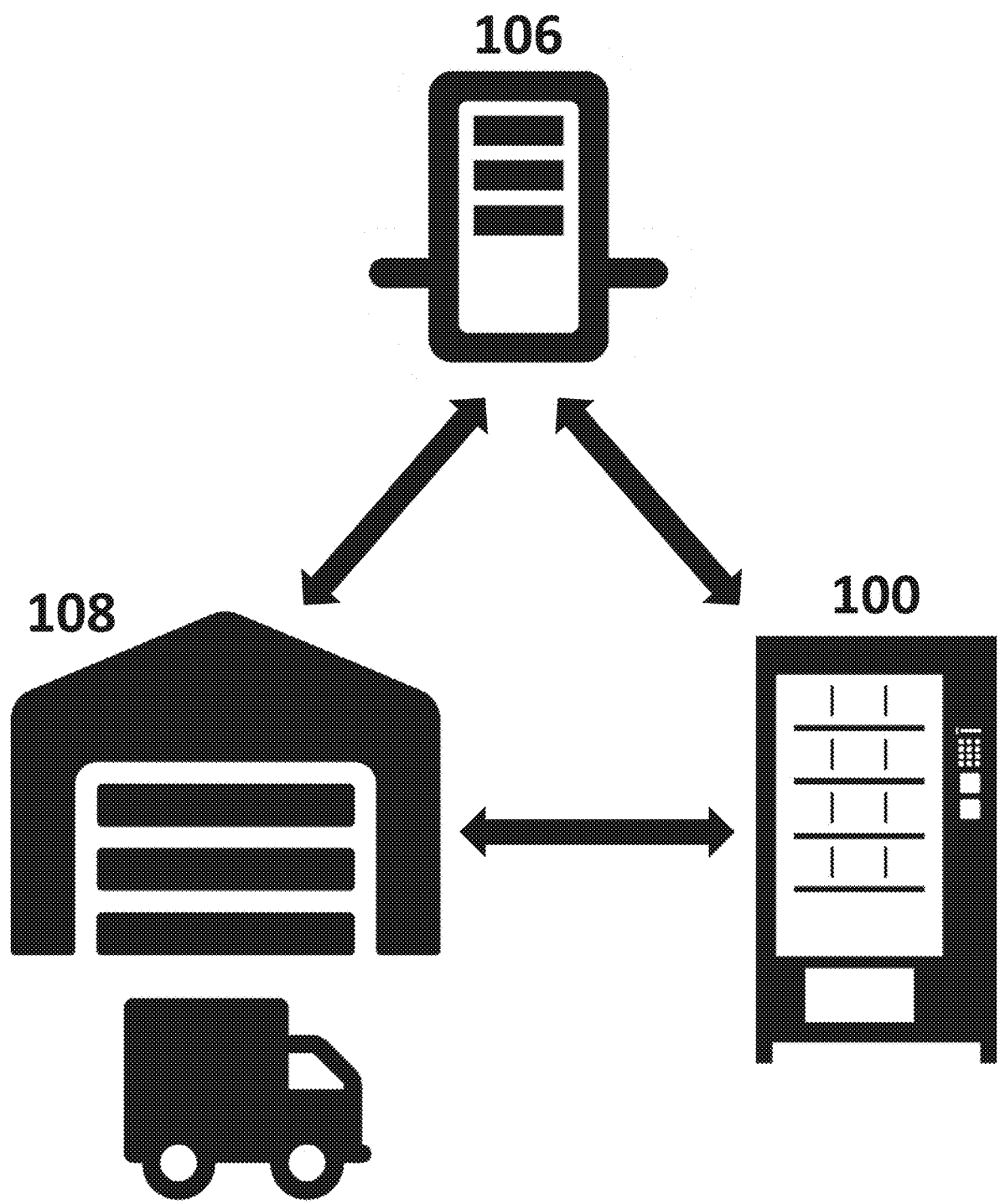

Referring now to FIG. 2a, showing a schematic representation of an exemplary basic pharmaceutical dispensing system, according to some embodiments of the invention. In some embodiments, the minimal requirement of a pharmaceutical dispensing system comprises a dispensing machine 100, a server 106 and a warehouse 108. In some embodiments, a dispensing machine is connected to a central server. In some embodiments, there is an exchange of information between the dispensing machine and the server, for example prescriptions, pharmaceutical inventories and technical status of the machine. In some embodiments, the server is also connected to a warehouse, which, according to instructions from the server, provides pharmaceuticals and/or technical assistance to the dispensing machine.

Figure 2B:
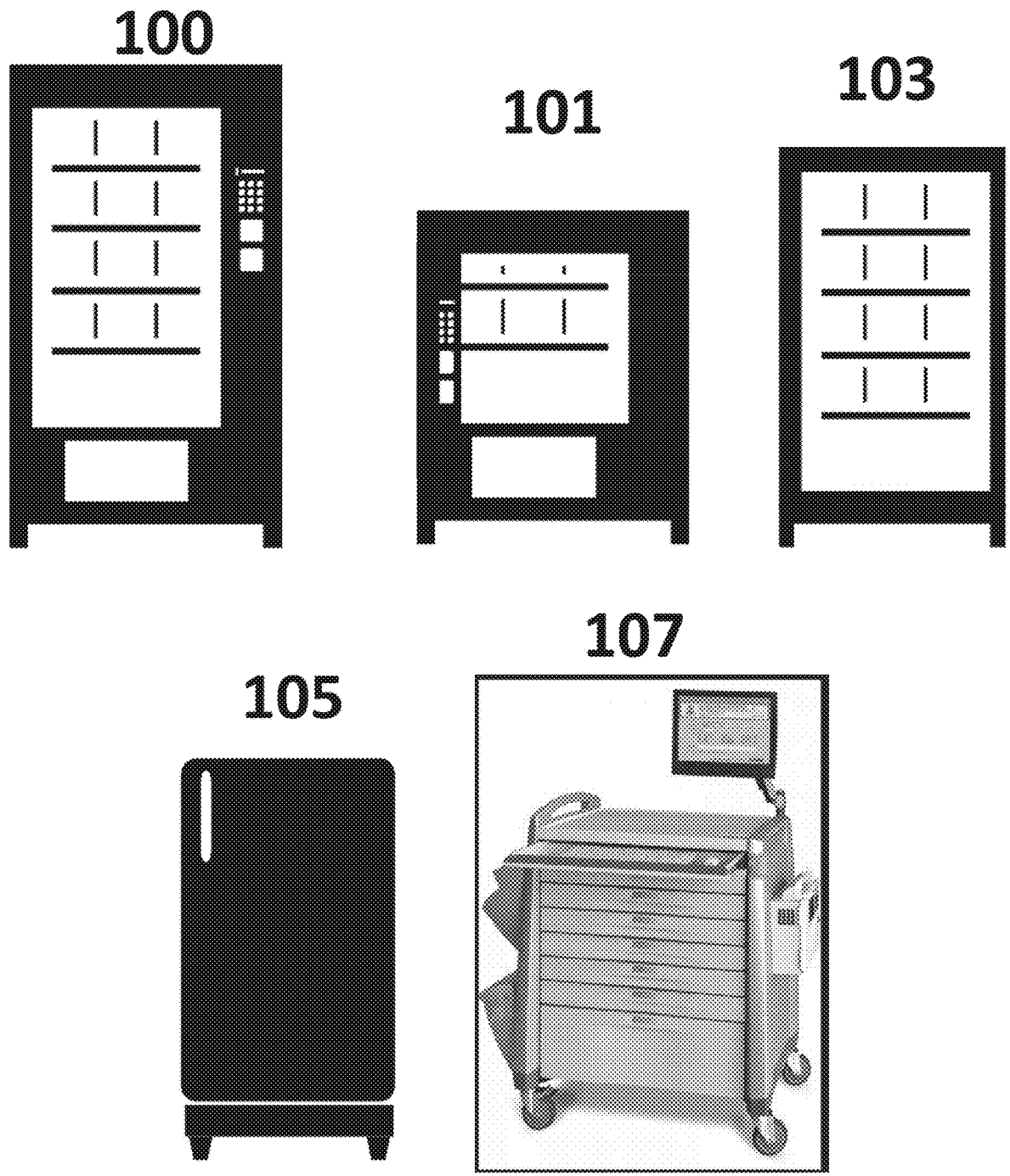

Referring now to FIG. 2b, showing a schematic representation of a variety of pharmaceutical machines (devices) used by the pharmaceutical dispensing system. In some embodiments, the pharmaceutical dispensing system comprises a plurality of devices that can be placed in the relevant locations. In some embodiments, one or more devices are placed in the same location. In some embodiments, a combination of devices are placed in the same location. In some embodiments, the devices are capable of storing and dispensing pharmaceuticals. In some embodiments, the devices only storage pharmaceuticals. In some embodiments, the device is a large dispensing machine 100. In some embodiments, the device is a small dispensing machine 101. In some embodiments, the device is a bulk storage cabinet 103. In some embodiments, the device is a refrigerator 105. In some embodiments, the device is a nursing cart 107.

In some embodiments, the large pharmaceutical dispensing machine 100 is adapted to store, package and dispense a large quantity of pharmaceuticals. In some embodiments, the small pharmaceutical dispensing machine 101 comprises the same capabilities of the large machine 100 but with fewer pharmaceuticals in it. In some embodiments, the bulk storage cabinet 103 comprises a variety of pharmaceuticals and medical materials (e.g. liquid drugs, IV, bandages, insulin, pill storage) in bulk. In some embodiments, the small and/or the large pharmaceutical dispensing machine packages pharmaceuticals as the circumstance arises (also known as PRN—"pro renata") and/or first dose pharmaceuticals for a single patient. In some embodiments, adapted and authorized personnel can access the bulk storage cabinet 103 when necessary. In some embodiments, the refrigerator 105 comprises a variety of pharmaceuticals and/or medical materials that require special storage temperatures. In some embodiments, adapted and authorized personnel can access the refrigerator 105 when necessary. In some embodiments, the nursing cart 107 are locked and opened by adapted and authorized personnel.

In some embodiments, any of the above dispensing machines and/or storage units assists in the pharmaceutical dispensing service. In some embodiments, different devices of the system are used in combination to provide the pharmaceuticals in the pharmaceutical dispensing service. In some embodiments, each of the abovementioned devices is monitored and controlled by the system.

In some embodiments, any of the above dispensing machines and/or storage units comprise a plurality of pharmaceuticals according to their physical capacities, for example, certain dispensing machine may comprise 30 different pharmaceuticals, while other may comprise 100 or 300 or any quantity of different pharmaceuticals.

Exemplary Interactions in a Pharmaceutical Dispensing System

In some embodiments, the pharmaceutical dispensing system coordinates the interactions between the pharmaceutical dispensing system and other machines and/or systems and/or facilities. In some embodiments, a specific pharmaceutical dispensing system (e.g. a dispensing machine) may require support (i.e. technical assistance and/or refilling and/or emergency supply). In some embodiments, support is provided from another pharmaceutical dispensing system (e.g. another dispensing machine).

In some embodiments, units of the pharmaceutical dispensing system are also defined by a relative physical distance and/or a relative period of time between them. In some embodiments, the relative physical distance is from about 0 kilometers to about 500 kilometers. Optionally, the relative physical distance is from about 50 kilometers to about 300 kilometers. Optionally, the relative physical distance is from about 100 kilometers to about 200 kilometers. In some embodiments, the relative period of time required to move from one pharmaceutical dispensing system to another is from about 0 minutes to about 48 hours. Optionally, the relative period of time required to move from one pharmaceutical dispensing system to another is from about 30 minutes to about 24 hours. Optionally, the relative period of time required to move from one pharmaceutical dispensing system to another is from about 2 hours to about 12 hours.

In some embodiments, depending on the nature of the problem (e.g. technical malfunction, refilling) and the level of urgency, the system activates a unit in the pharmaceutical dispensing system (e.g. a dispensing machine) according to the distance and/or the time required to reach the dispensing machine in trouble. In some embodiments, the time of preparation of the pharmaceuticals before the dispensing and/or the time of the dispensing itself are also taken under consideration when choosing which unit to activate. For example, a dispensing machine stopped working and the next scheduled round of dispensing pharmaceuticals is in 3 hours. At this point, the system activates the closest dispensing machine that is equipped to provide the required pharmaceuticals. Another example, if the next scheduled round of dispensing pharmaceuticals is in 10 hours, but the time for a technician to arrive is 3 hours, the system will activate the technician instead of requesting pharmaceuticals from a different dispensing machine.

In some embodiments, the parameter that guides which unit is activated is the assurance that the patients will receive the pharmaceuticals on time. In some embodiments, the parameter that guides which unit is activated is the request from a single and/or multiple dispensing machines to the potential provider of pharmaceuticals and/or technical assistance.

Exemplary different interactions will be described in the following paragraphs.

Exemplary On-Site Second System (On-Site Interaction Layer)

Figure 3:
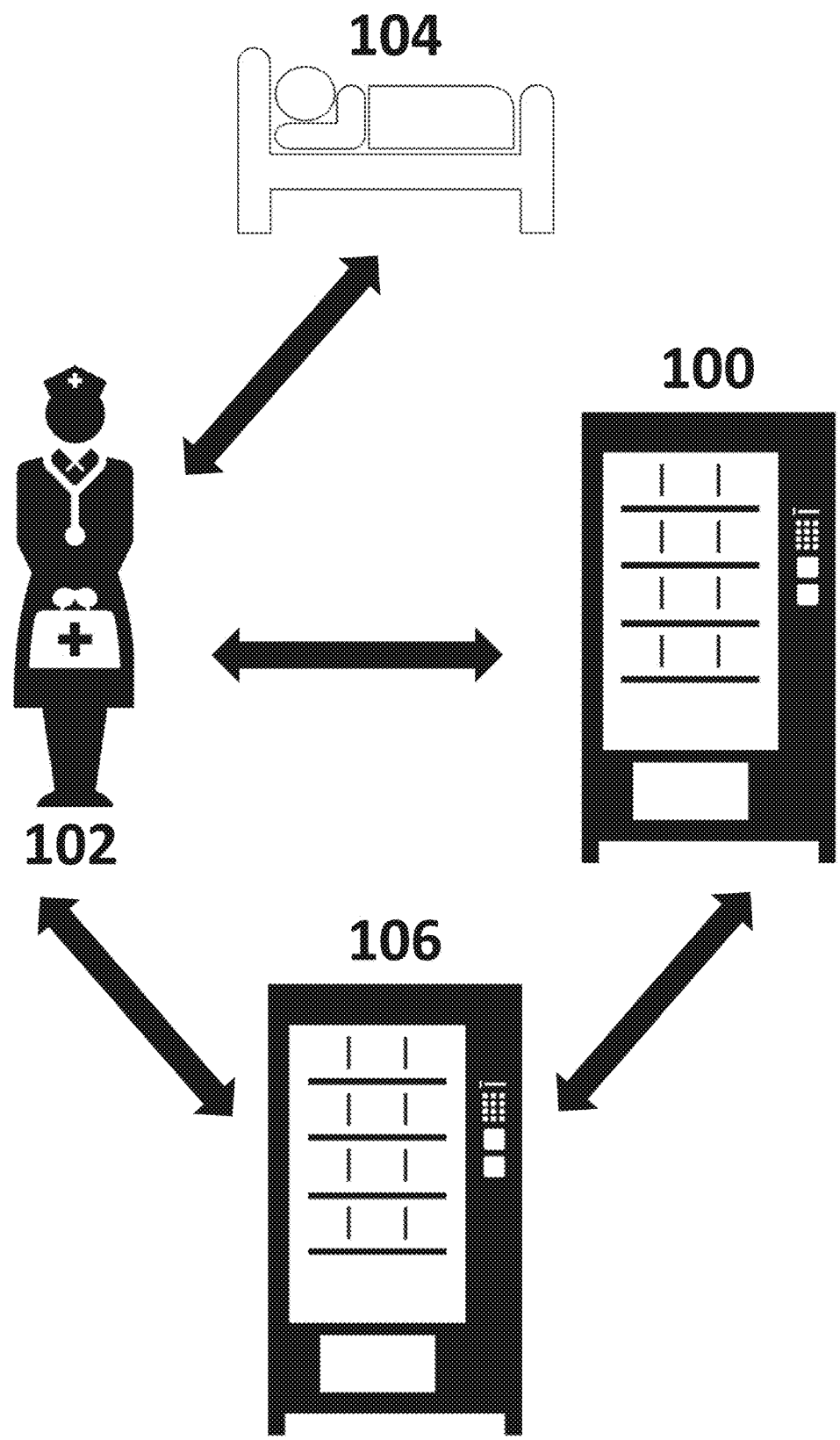
FIG. 3 is a schematic representation of an on-site pharmaceutical dispensing system, according to some embodiments of the invention.

In some embodiments, the pharmaceutical dispensing system comprises at least two dispensing machines located in the same site (e.g. long term care facility). Referring now to FIG. 3, showing a schematic representation of an on-site pharmaceutical dispensing system. In some embodiments, the on-site system comprises at least two dispensing machines 100-106, in communication with each other by conventional means (e.g. wire, wireless) and in communication with the server 106 (not shown). In some embodiments, the personnel 102 of the long term care facility may access each dispensing machine and provide pharmaceuticals to the patients 104.

In some embodiments, the dispensing machines located at the same site are identical to each other in their capabilities to store and dispense pharmaceuticals. In some embodiments, the dispensing machines located at the same site are different to each other in their capabilities to store and dispense pharmaceuticals. In some embodiments, one of the dispensing machines is a main dispensing machine, comprising the necessary pharmaceuticals required for the long term facility, while the other dispensing machine is a secondary dispensing machine comprising some of the necessary pharmaceuticals required for the long term facility. In some embodiments, if one of the two dispensing machines is unable to fulfill its purpose, then the second dispensing machine "covers" for the purpose of both dispensing machines until the first dispensing machine is returned to normal function. This enables a continue cover of the pharmaceutical dispensing requirements of the long term facility almost without the necessity to involve the long term facility personnel.

For example, a facility comprises a large dispensing machine 100 and a small dispensing machine 101. In some embodiments, the two machines work in coordination with each other to provide pharmaceutical dispensing service to the facility. Optionally, any combination of two machines (large dispensing machine 100, a small dispensing machine 101, bulk storage cabinet 103, a refrigerator 105 and/or a nursing cart 107) apply to this example. In some embodiments, if either of the machines cannot provide the dispensing service, the second machine fulfills the required service for both machines.

Exemplary Off-Site Second System (Off-Site Interaction Layer—Second System)

Figure 4:
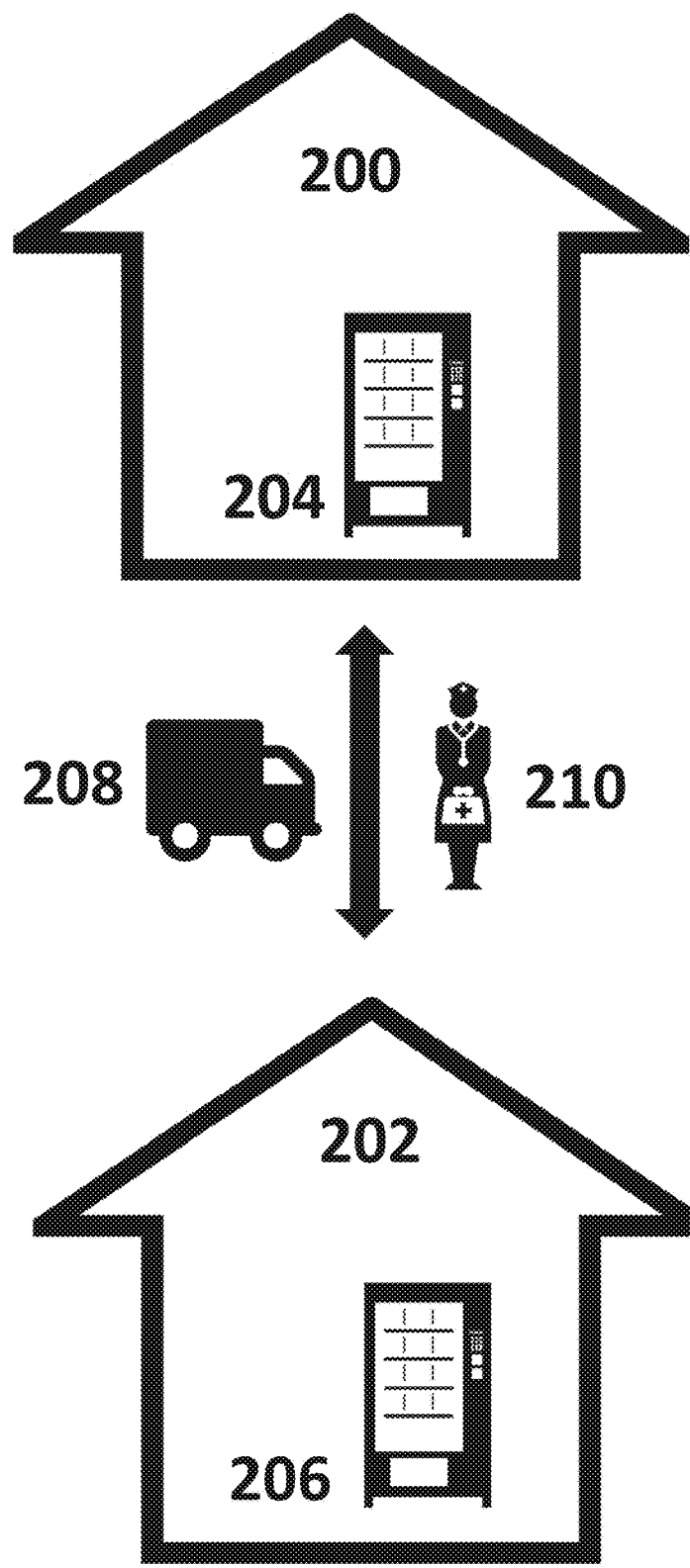
FIG. 4 is an exemplary schematic representation of the interaction between a long term facility and a secondary off-site location having a second pharmaceutical dispensing system, according to some embodiments of the invention.

Referring now to FIG. 4, showing an exemplary schematic representation of the interaction between a long term facility 200 and a secondary off-site location 202 having a second pharmaceutical dispensing system 206. In some embodiments, if the dispensing machine 204 located at the long term facility 200 requires assistance, for example due to a malfunction and/or lack of inventory (or any other reason) and cannot supply, either partially or completely, the required pharmaceuticals, the dispensing machine 204 contacts the server (not shown) and makes an automatic request. In some embodiments, the server activates a second dispensing machine 206 located at another site 202, which is capable of supplying the required, either all or partially, pharmaceuticals without affecting the performance requirements of its own site. In some embodiments, the movement of pharmaceuticals from one site to the other is performed by dedicated transportation units 208 sent by the system. In some embodiments, the movement of pharmaceuticals from one site to the other is performed by the personnel 210 of either facility. In some embodiments, the secondary dispensing device will provide assistance as long as is necessary.

In some embodiments, the secondary off-site location 202 is located in close proximity of the long term facility 200. In some embodiments, close proximity is defined as travel time to the long term facility from about 0 minutes to about 20 hours. Optionally from about 2 hours from about 12 hours. Optionally from about 4 hours to about 8 hours. In some embodiments, close proximity is defined as travel distance to the long term facility from to about 0 kilometers to about 1000 kilometers. Optionally, from about 50 kilometers to about 500 kilometers. Optionally from about 100 kilometers to about 300 kilometers.

Exemplary Off-Site Main System (Off-Site Interaction Layer—Main System)

Figure 5:
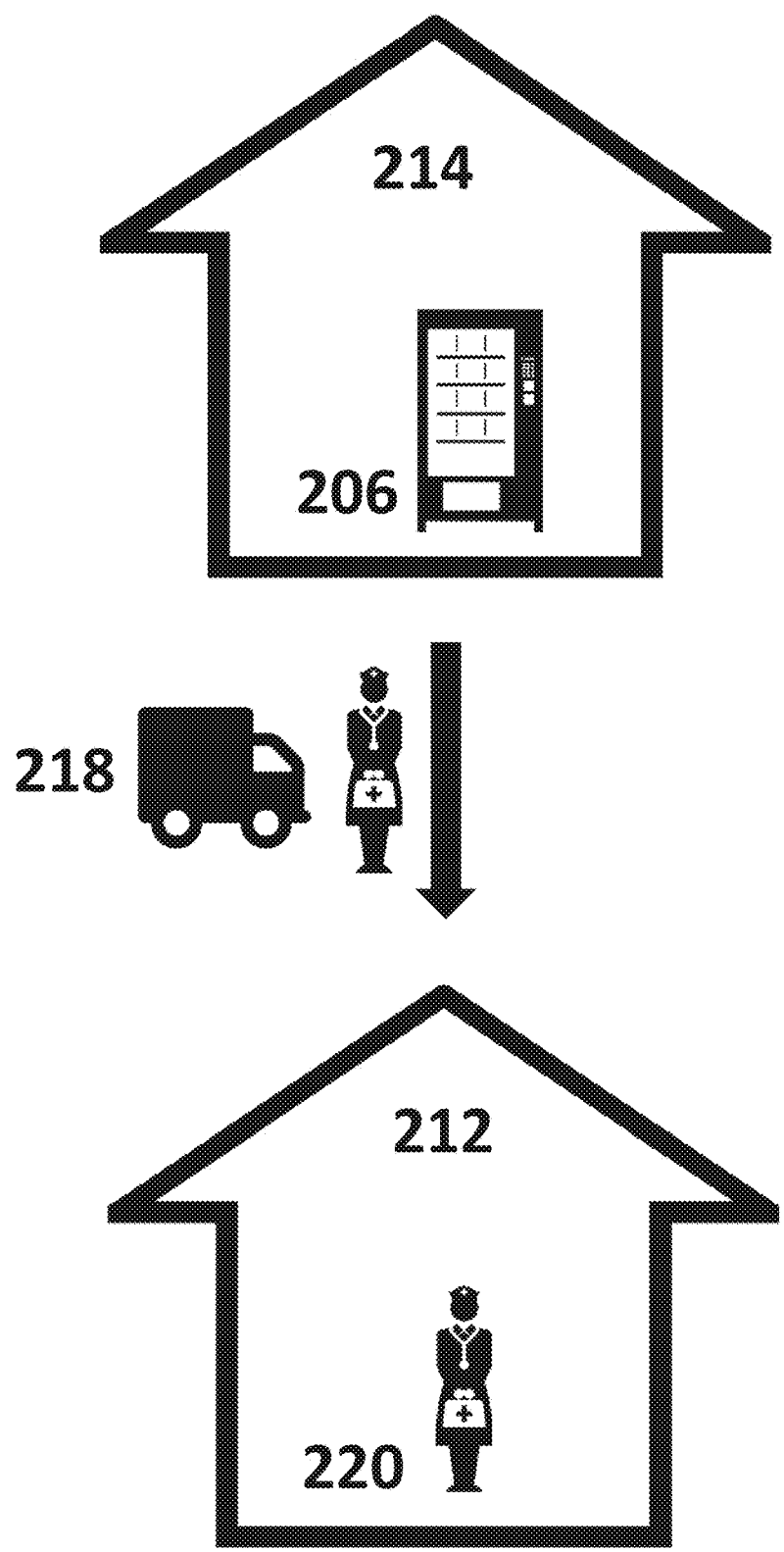
FIG. 5 is a schematic representation of an off-site main system and its interaction with a site without a dispensing machine, according to some embodiments of the invention.

Referring now to FIG. 5, showing a schematic representation of an off-site main system and its interaction with a site without a dispensing machine. In some embodiments, a first location 212 may not comprise a dispensing machine of their own. In some embodiments, storage, preparation of pharmaceuticals and dispensing is performed in an off-site location 214 having a pharmaceutical dispensing system and dispensing machine 216 and delivered 218 to the personnel 220 at the first location 212. In some embodiments, the first location 212 comprises a dedicated user interface unit (i.e. a dedicated online website view from a regular computer or a dedicated interface unit) from which the necessary communications with the system, through a server, are performed.

Exemplary Off-Site Distant Second System (Off-Site Interaction Layer—Distant Second System)

Figure 6:
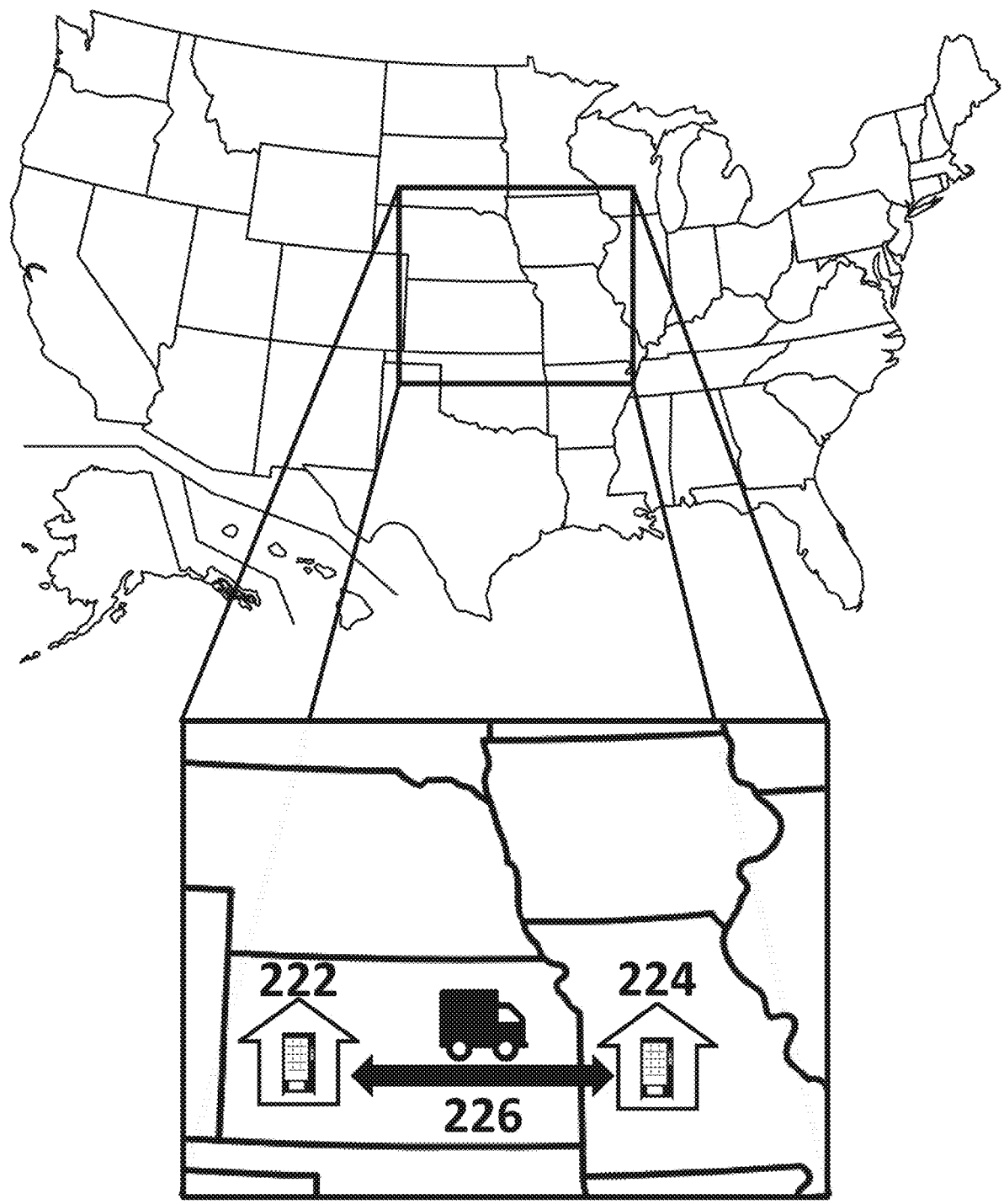
FIG. 6 is an exemplary schematic representation of the interaction between a long term facility and a secondary distant off-site location having a second pharmaceutical dispensing system, according to some embodiments of the invention.

Referring now to FIG. 6, showing an exemplary schematic representation of the interaction between a long term facility 222 and a secondary distant off-site location 224 (e.g. in another state) having a second pharmaceutical dispensing system. In some embodiments, if the dispensing machine located at the long term facility 222 requires assistance, for example due to a malfunction and/or lack of inventory (or any other reason), the dispensing machine located at the long term facility 222 contacts the server and performs an automatic request. In some embodiments, the server will analyze the request and activate a second dispensing machine located at another site 224 is capable of supplying the required pharmaceuticals without affecting the performance requirements of its own site. In some embodiments, the movement of pharmaceuticals from one site to the other is performed by dedicated transportation units 226 sent by the system. In some embodiments, the movement of pharmaceuticals from one site to the other is performed by the personnel 210 of either facility. In some embodiments, the secondary dispensing device will provide assistance as long as is necessary.

In some embodiments, the secondary distant off-site location 222 is not located in close proximity of the long term facility 224. In some embodiments, assistance from distant long term facilities and/or dispensing machines is activated only when there is no other facility closer to the one that requires assistance, and/or when the assistance is not urgent and a delayed arrival of assistance will not incur a miss in the dispensing of the pharmaceuticals to the patients. In some embodiments, not in close proximity is defined as travel time to the long term facility of about 24 hours or more. In some embodiments, not in close proximity is defined as travel distance to the long term facility of about 1000 kilometers or more.

Exemplary Off-Site Outside the System (Off-Site Interaction Layer—Outside the System)

Figure 7:
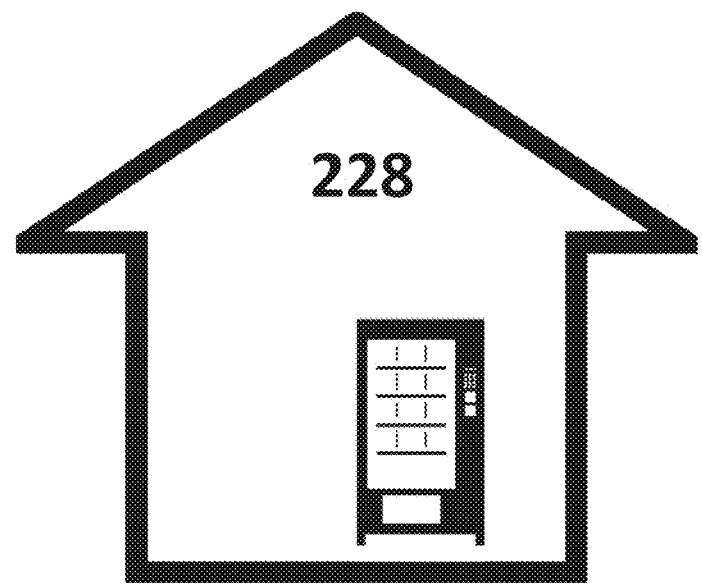
FIG. 7 is an exemplary schematic representation of the interaction between a long term facility and a pharmacy, according to some embodiments of the invention.
Figure 7:
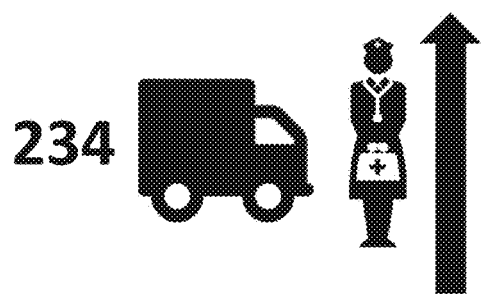
Figure 7:
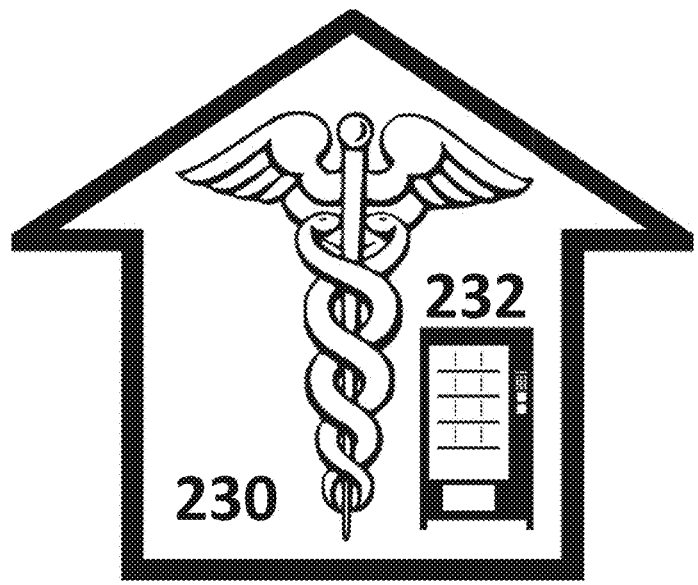

Referring now to FIG. 7, showing an exemplary schematic representation of the interaction between a long term facility 228 and a pharmacy 230. The pharmacy 230 is an entity outside the pharmaceutical dispensing system. In some embodiments, the pharmacy 230 may include a dispensing machine 232 which belongs to the pharmaceutical dispensing system. In some embodiments, the pharmacy does not include a dispensing machine. In some embodiments, when a dispensing machine located at the long term facility 228 requires assistance, for example due to a malfunction and/or lack of inventory (or any other reason), the dispensing machine located at the long term facility 228 communicated with the server and performs an automatic request. In some embodiments, the server activates a pharmacy 230, which either includes a dispensing machine 232 or not, and which is capable of supplying the required pharmaceuticals without affecting the performance requirements of its own site. In some embodiments, the movement of pharmaceuticals from the pharmacy 230 to the long term facility 228 is performed by dedicated transportation units 234 sent by the system. In some embodiments, the movement of pharmaceuticals from one site to the other is performed by the personnel of either facility. In some embodiments, the pharmacy will provide assistance as long as is necessary.

In some embodiments, the activation of a pharmacy to supply assistance is done when no other dispensing machine is in close proximity and when the urgency of the delivery is high (i.e. providing pharmaceuticals to the patients on time).

Exemplary Pharmaceutical Dispensing Ecosystem

The general use of the word ecosystem means "a complex network or interconnected system". Referring now to FIG. 8a, showing a schematic representation of the possible interactions in a pharmaceutical dispensing ecosystem. In some embodiments, interactions between the dispensing machines, the facilities, the storage units 248, the server 244, the pharmacies 246, the different regions 240-242, are all part of the pharmaceutical dispensing ecosystem. Also shown in FIG. 8a is the possible activation of dedicated delivery services 250 used together with the tracking system. Referring now to FIG. 8b showing a schematic representation of an exemplary cascade of interactions. In some embodiments, the interaction begins with a first degree interaction between two dispensing machines within the same facility 241. In some embodiments, the interaction continues with a second degree interaction between facilities 243 in the vicinity to each other. In some embodiments, the interaction continues with a third degree interaction between facilities 245 that are not in the vicinity of each other. In some embodiments, the interaction continues with a fourth degree interaction between facilities and other units (i.e.

pharmacies, storage units) 247. In some embodiments, the order of the degrees of interactions depends on the distance between dispensing units. In some embodiments, the order of the degrees of interaction depends on the quickest response time. In some embodiments, the order of the degrees of interaction depends on the availability of the pharmaceuticals. In some embodiments, the order of the degrees of interaction depends on a combination of all of the above.

Exemplary Pharmaceutical Dispensing Methods

Figure 9:
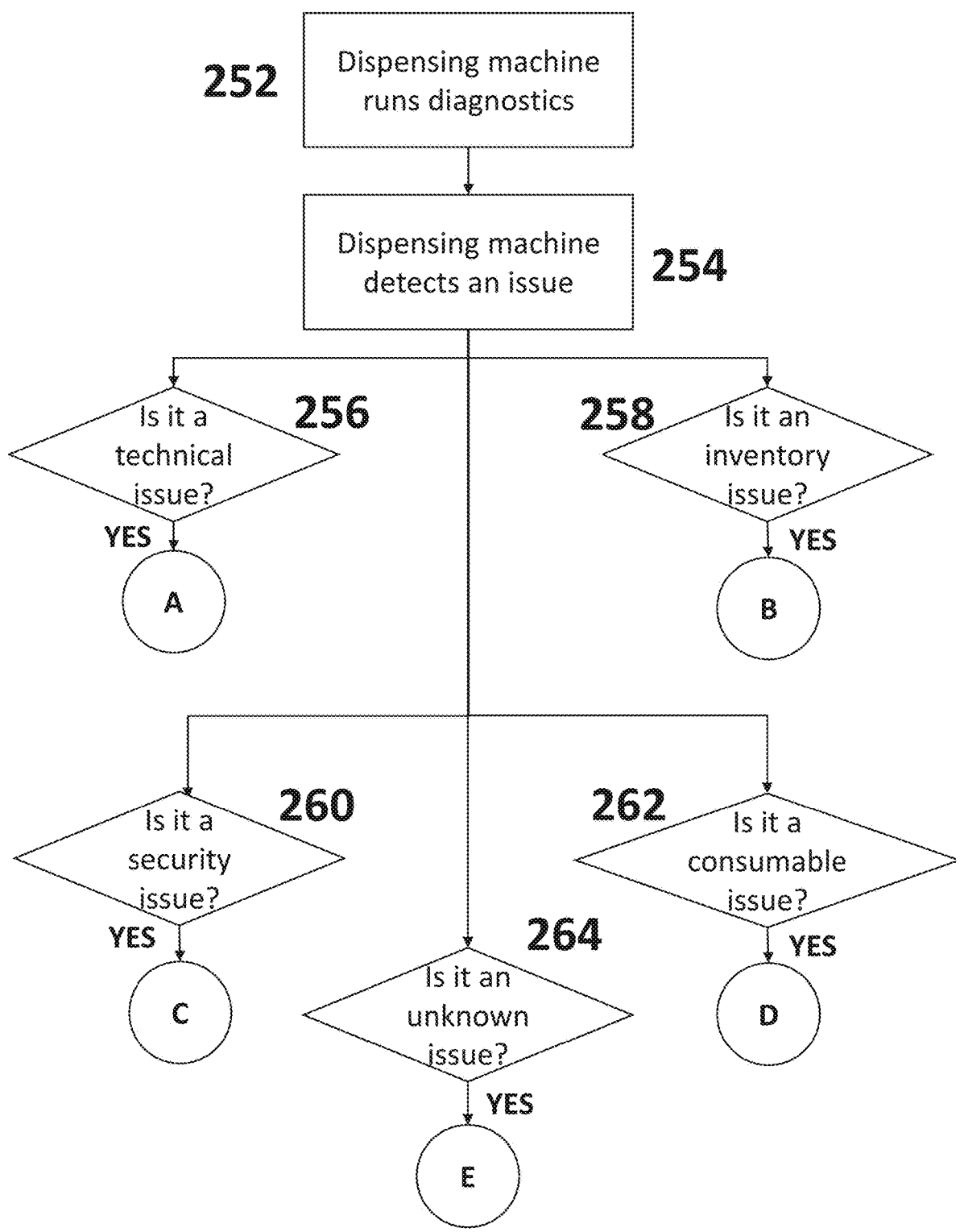
Figure 10:
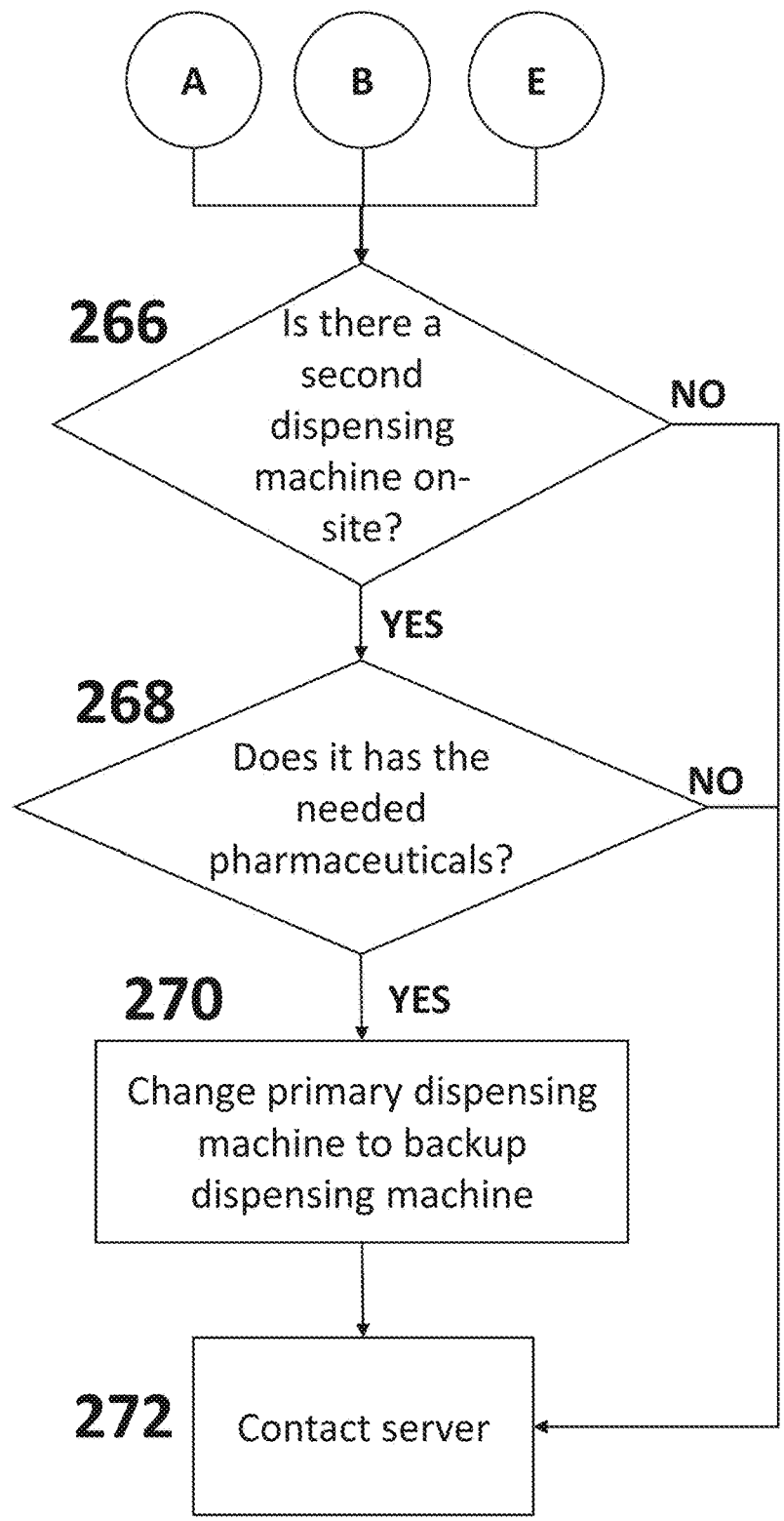
Figure 11:
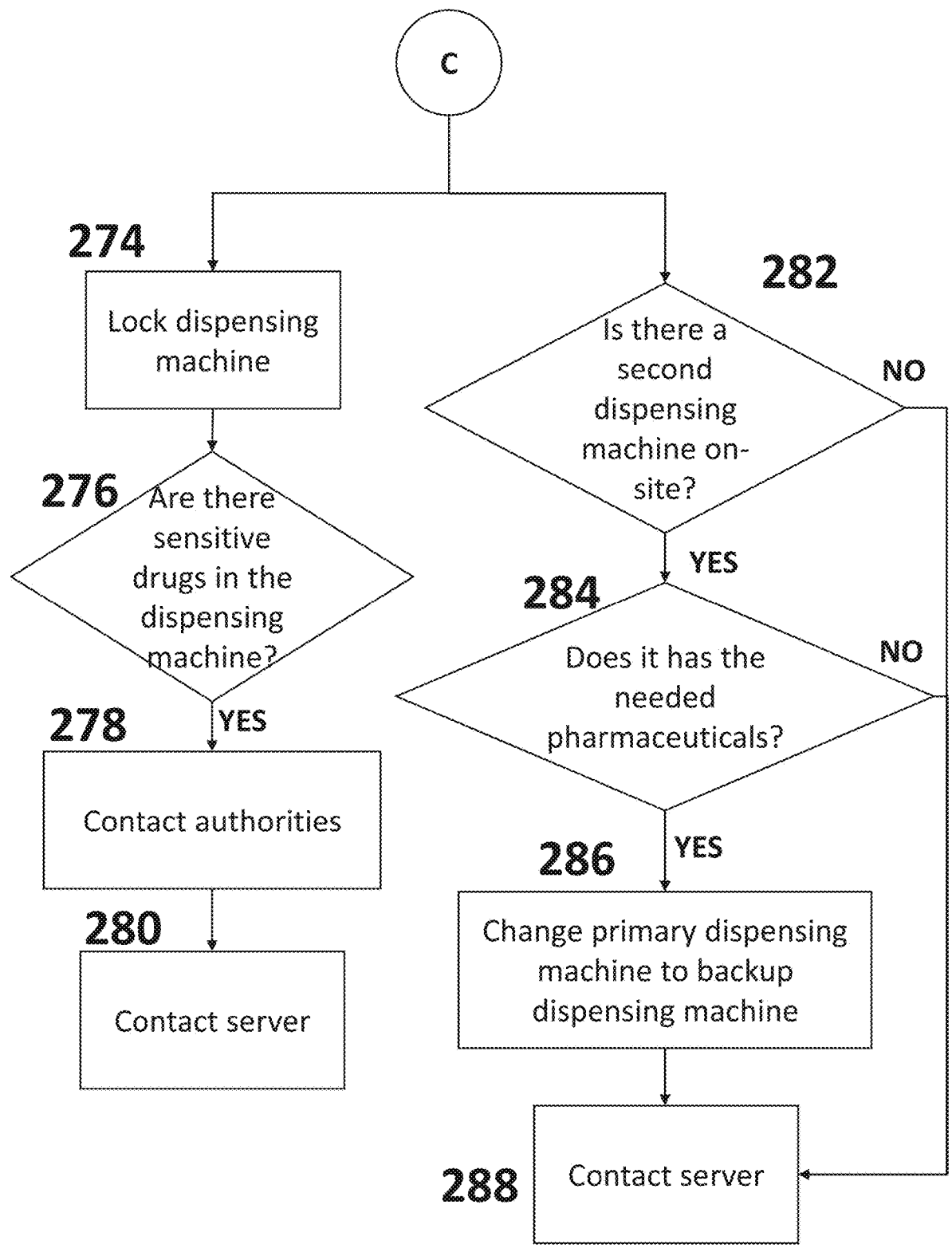
Figure 12:
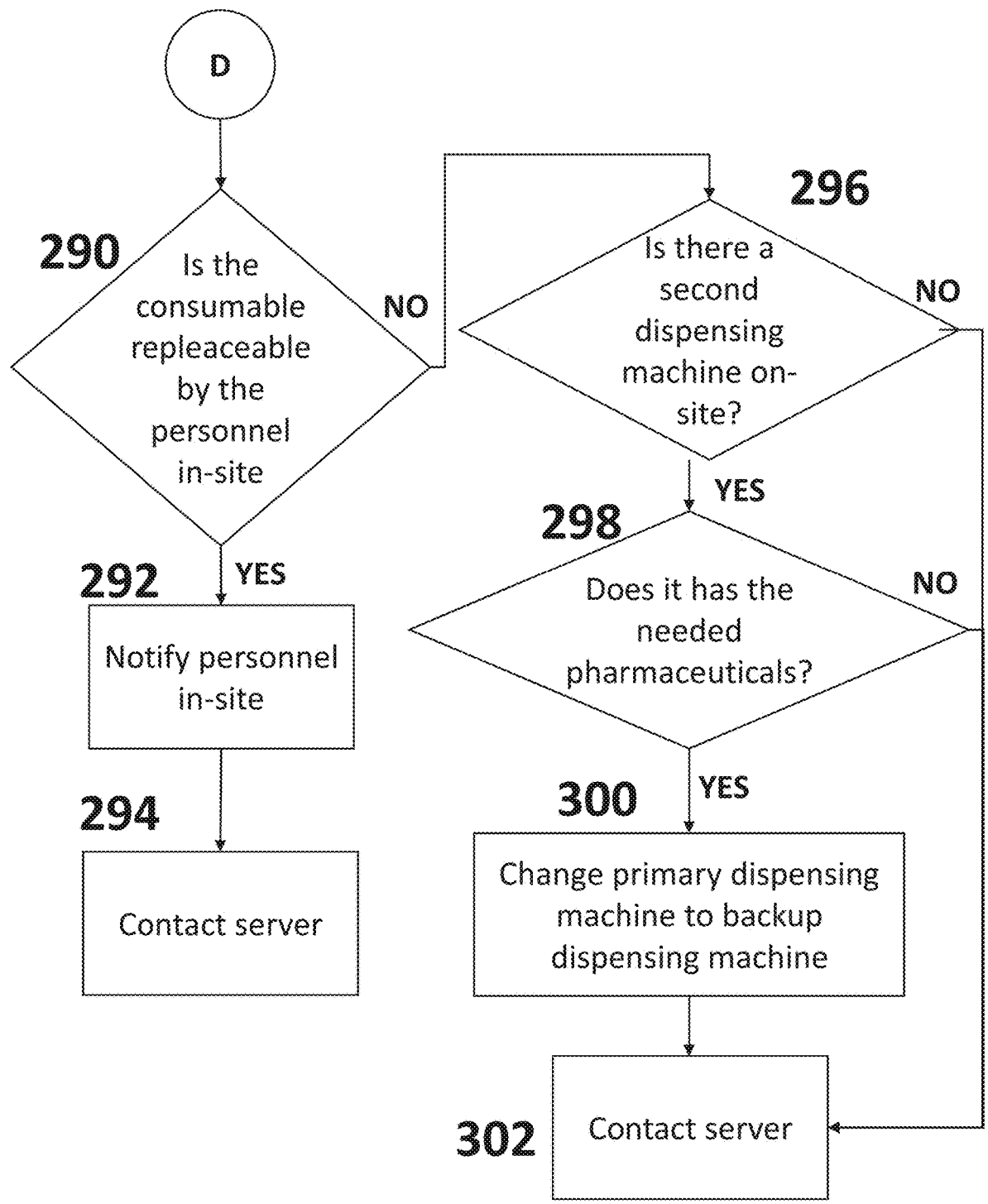

Referring now to FIG. 9, showing a schematic flowchart of one exemplary method of management and operations performed by the pharmaceutical dispensing system. In some embodiments, the dispensing machine runs a self-diagnostic program 252 on its software, hardware and inventory. In some embodiments, the dispensing machine might detect an issue 254 during the self-diagnostic program. In some embodiments, issues revealed by the self-diagnostic program might be, for example, a technical issue 256, an inventory issue 258 a security issue 260, a consumable issue 262 and/or an unknown issue 264. In some embodiments, a cascade of inquiries is activated in each of the scenarios in order to assess the situation and proceed accordingly, as will be explain in the following paragraph. In some embodiments, the dispensing machine continues the diagnostic program 262 until either it receives an "all ok" response or until an issue is detected and identified. In some embodiments, if the issue is a technical issue 256 and/or an inventory issue 258 and/or an unknown issue 264, then (Flowchart continues following the letters A, B and E to FIG. 10), the system assesses if there is a second dispensing machine on-site 266. In some embodiments, if there is, the system assesses if the second dispensing machine comprises the necessary pharmaceuticals for the correct dispensing in the long term facility 268. In some embodiments, if the second dispensing machine comprises the necessary pharmaceuticals, the system changes the primary dispensing machine to the back-up dispensing machine 270, and contacts the server to communicate the issue 272. In some embodiments, if the second dispensing machine does not comprise the necessary pharmaceuticals, the system contacts the server to communicate the issue 272. In some embodiments, if there is not a second dispensing machine on-site, the system contacts the server to communicate the issue 272.

In some embodiments, if the issue is a security issue 260, then (Flowchart continues following the letter C to FIG. 11), then the system commences two independent actions. In some embodiments, the system locks the machine 274 and assesses if there are sensitive drugs in the dispensing machine 276. In some embodiments, if there are sensitive drugs, then the system contact the authorities (i.e. police) 278 and contact the server to communicate the issue 280. In some embodiments, the second action is to assess if there is a second dispensing machine on-site 282. In some embodiments, there is, the system assesses if the second dispensing machine comprises the necessary pharmaceuticals for the correct dispensing in the long term facility 284. In some embodiments, if the second dispensing machine comprises the necessary pharmaceuticals, the system changes the primary dispensing machine to the back-up dispensing machine 286, and contacts the server to communicate the issue 288. In some embodiments, if the second dispensing machine does not comprise the necessary pharmaceuticals, the system contacts the server to communicate the issue 288. In some embodiments, if there is not a second dispensing machine on-site, the system contacts the server to communicate the issue 288.

In some embodiments, if the issue is a consumable issue 262, then (Flowchart continues following the letter D to FIG. 12), then the system assesses if the consumable is replaceable by the personnel in-site (i.e. nurse) 290. In some embodiments, if the answer is yes, the system notifies the personnel 292 that a consumable needs to be replaced and/or refilled, and then system contacts the server to communicate the issue 294. In some embodiments, if the consumable is not replaceable by the personnel, then the system assesses if there is a second dispensing machine on-site 296. In some embodiments, there is, the system assesses if the second dispensing machine comprises the necessary pharmaceuticals for the correct dispensing in the long term facility 298. In some embodiments, if the second dispensing machine comprises the necessary pharmaceuticals, the system changes the primary dispensing machine to the back-up dispensing machine 300, and contacts the server to communicate the issue 302. In some embodiments, if the second dispensing machine does not comprise the necessary pharmaceuticals, the system contacts the server to communicate the issue 302. In some embodiments, if there is not a second dispensing machine on-site, the system contacts the server to communicate the issue 302.

In some embodiments, issues may be detected by the personnel of the long term facility. In some embodiments, the personnel of the long term facility may communicate the issues directly to the server by entering the relevant information, either through the control panel of the dispensing machine or through a dedicated website using a regular computer and/or smartphone and/or tablet.

Figure 13:
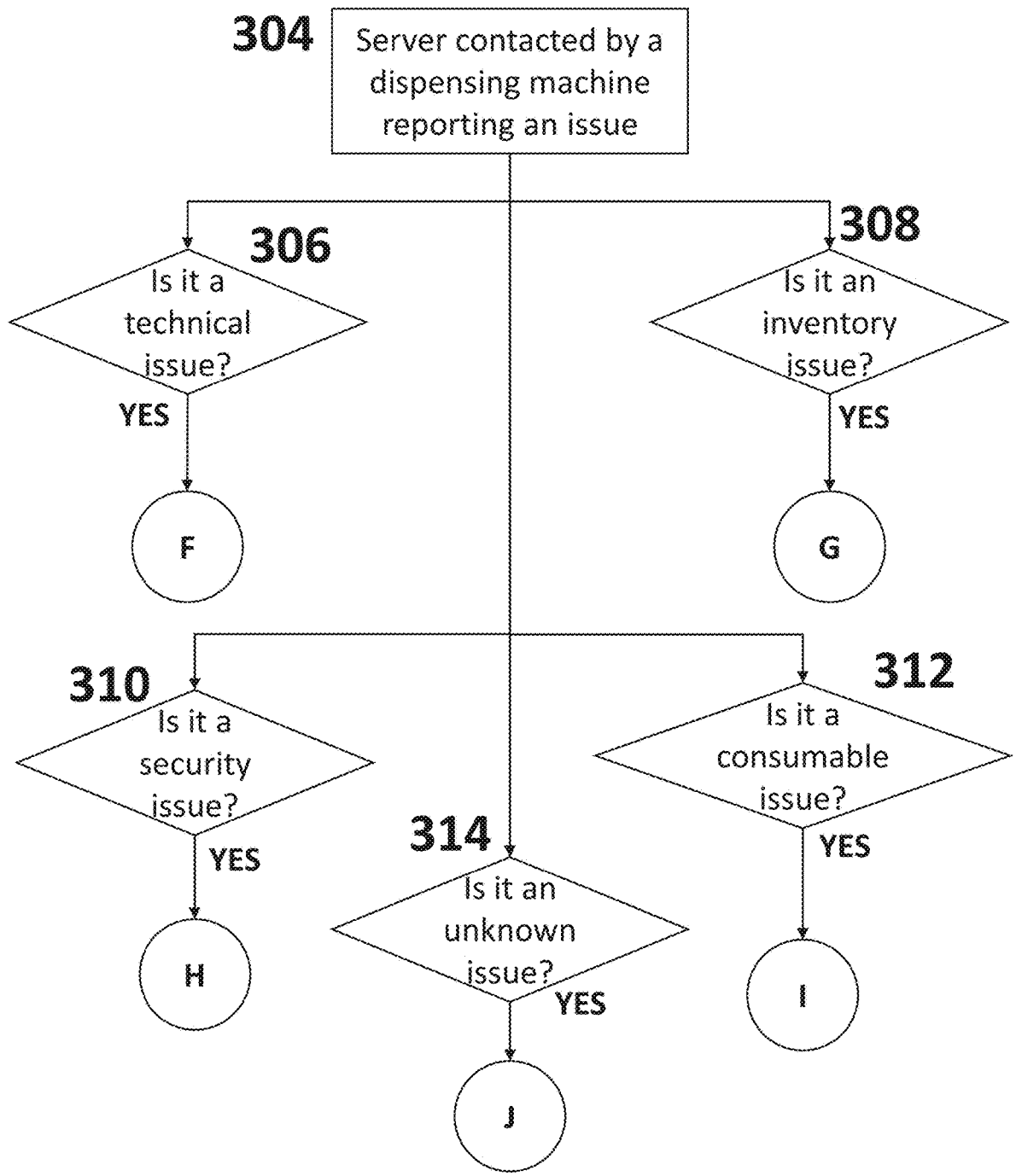
Figure 14:
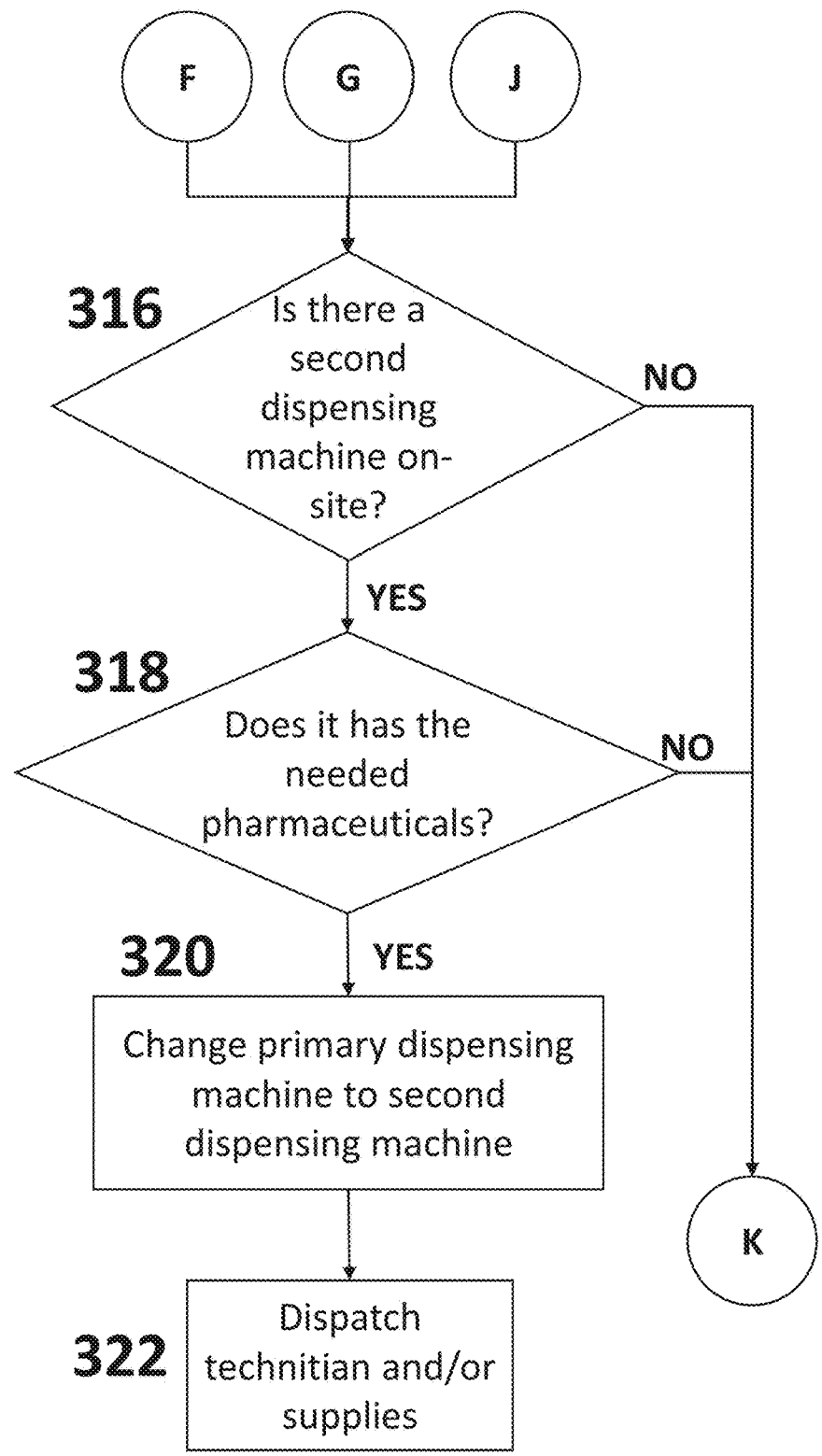
Figure 15:
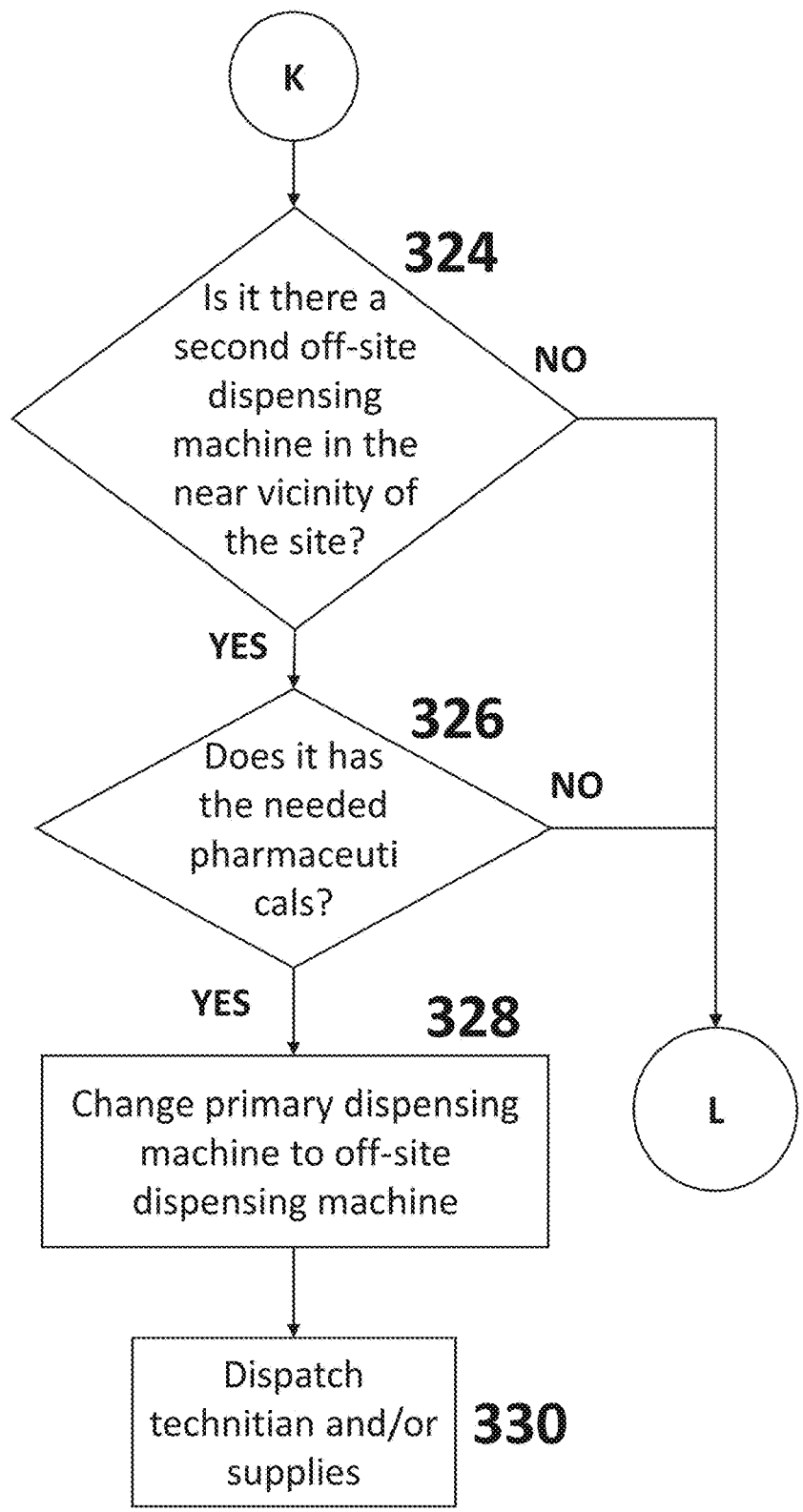
Figure 16:
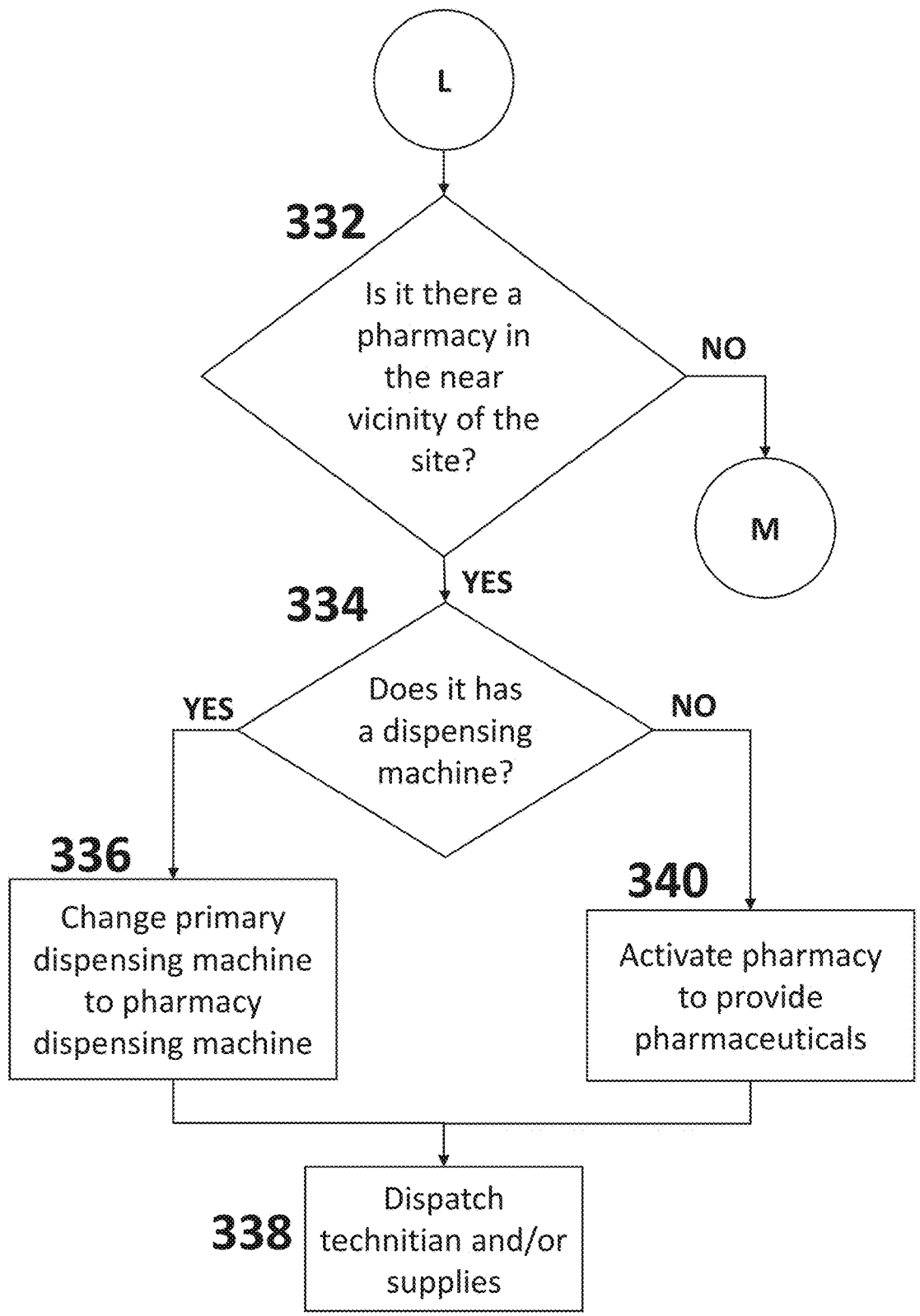
Figure 17:
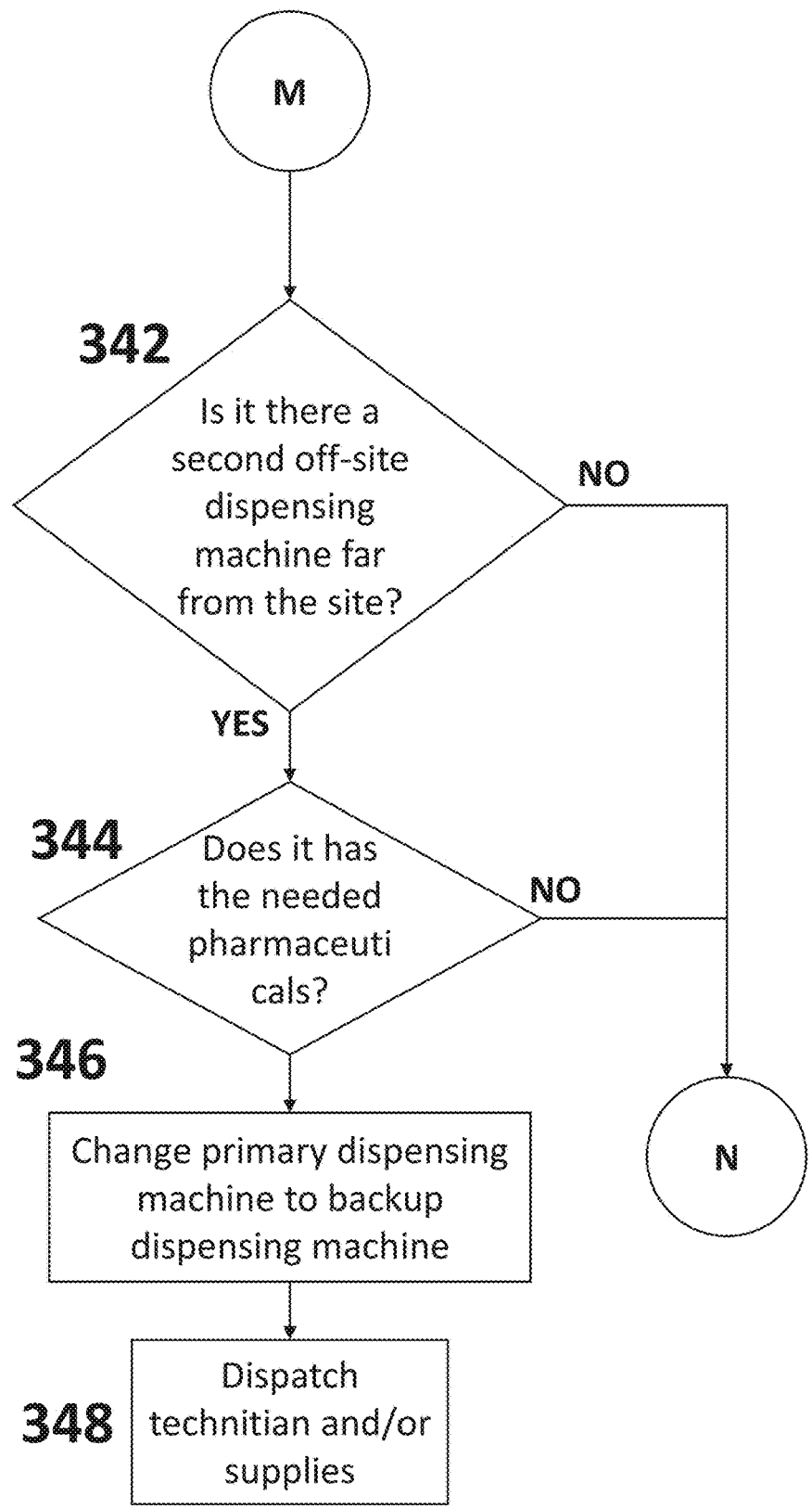
Figure 18:
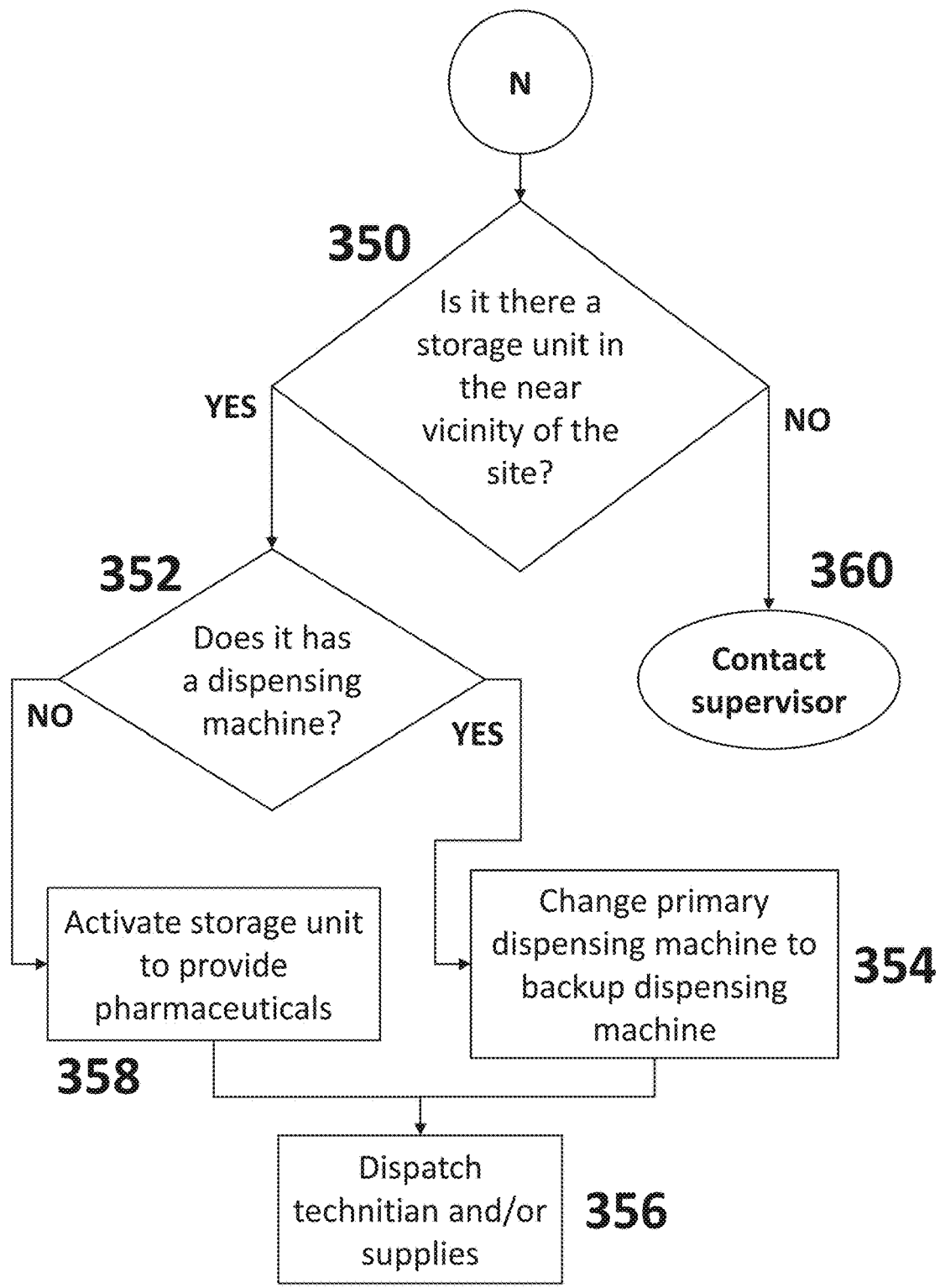
Figure 19:
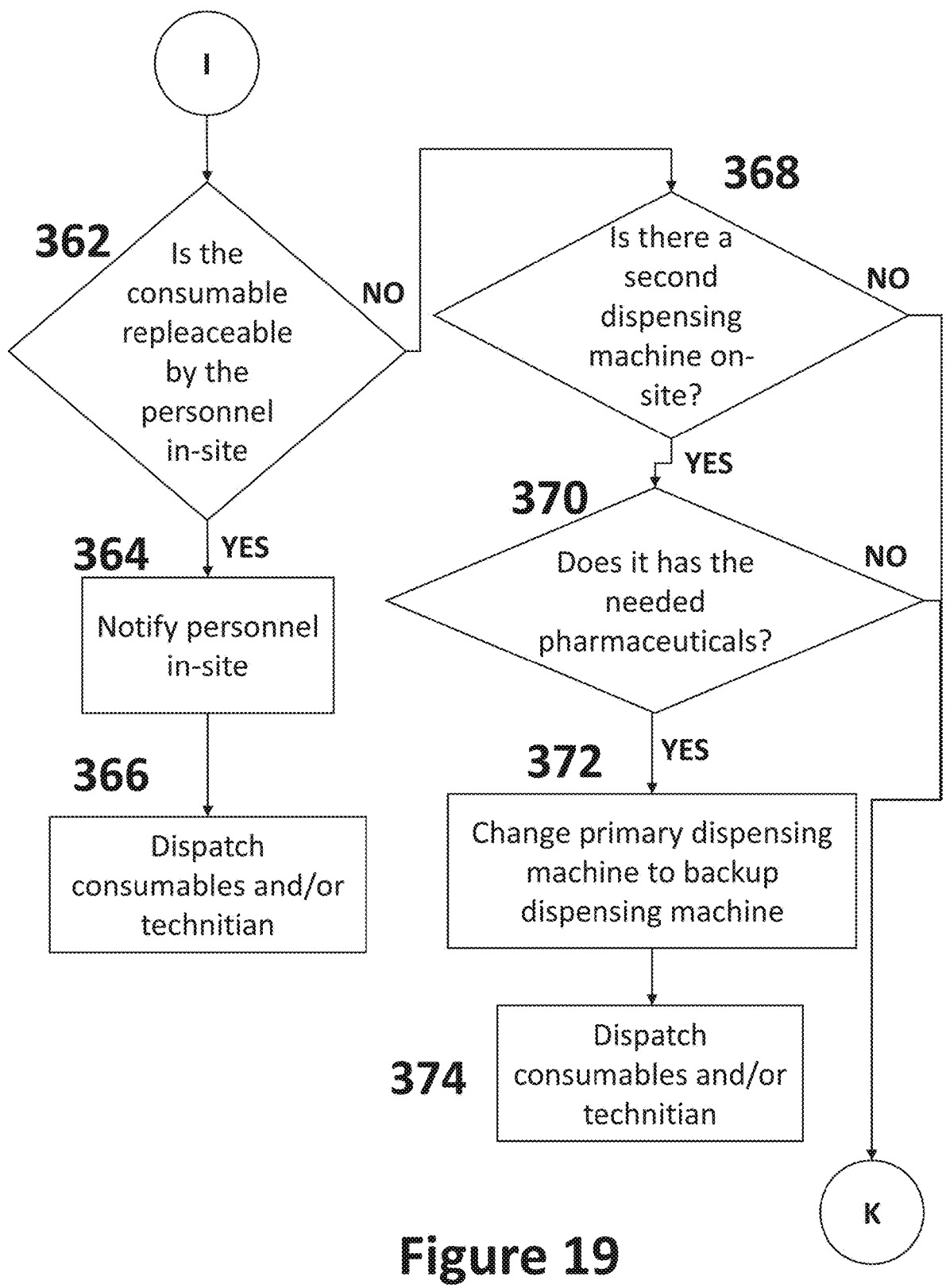
Figure 20:
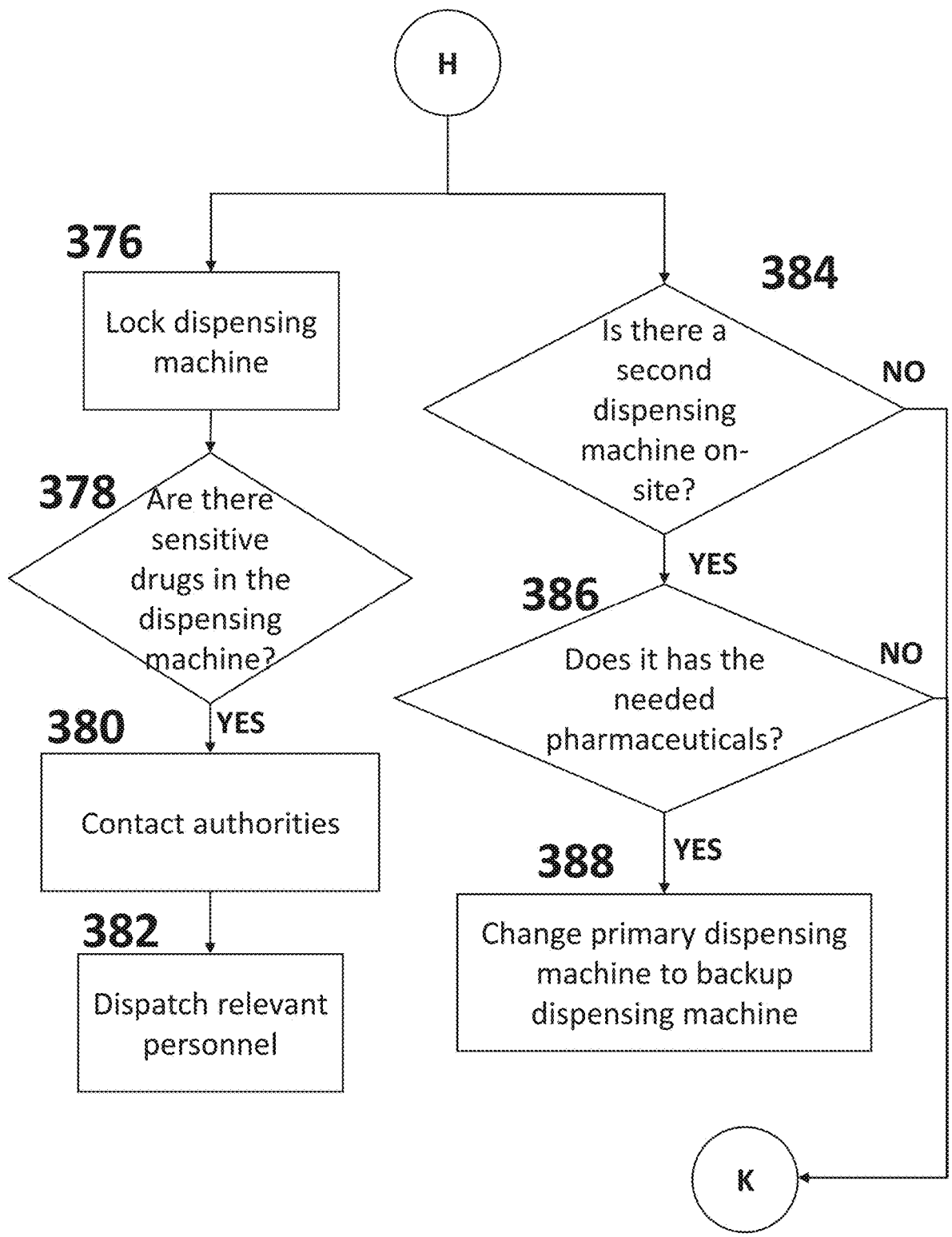

Referring now to FIG. 13, showing a schematic flowchart of a method performed by an exemplary server of the pharmaceutical dispensing system. In some embodiments, the server is contacted by a dispensing machine reporting an issue 304. In some embodiments, the server assesses what kind of issue is reported by the dispensing machine, for example, a technical issue 306, an inventory issue 308, a security issue 310, a consumable issue 312 and/or an unknown issue 314. In some embodiments, a cascade of inquiries is activated in each of the scenarios in order to assess the situation and proceed accordingly, as will be explain in the following paragraph. In some embodiments, if the issues are related to technical issues 306, inventory issues 308 and/or an unknown issue 310, then (Flowchart continues following the letters F, G and J to FIG. 14) the servers first assesses if there is a second dispensing machine on-site 316. In some embodiments, if the answer is yes, then the server assesses if the second dispensing machine comprises the necessary pharmaceuticals for the correct dispensing in the long term facility 318. In some embodiments, if the second dispensing machine comprises the necessary pharmaceuticals, the system changes the primary dispensing machine to the second dispensing machine as the primary dispensing machine of the long term facility 320, and dispatches a technician and/or dispatches pharmaceuticals supplies to the long term facility to assess and repair the issue and/or to resupply the missing pharmaceuticals 322. In some embodiments, if there is not a second on-site dispensing machine, then (Flowchart continues following the letter K to FIG. 15) the server assesses if there is a second dispensing machine off-site 324 in the vicinity of the long term facility. In some embodiments, if the answer is yes, then the server assesses if the second off-site dispensing machine comprises the necessary pharmaceuticals for the correct dispensing in the long term facility 326. In some embodiments, if the second off-site dispensing machine comprises the necessary pharmaceuticals, the system changes the primary dispensing machine to the second off-site dispensing machine as the primary dispensing machine of the long term facility 328, and dispatches a technician and/or dispatches pharmaceuticals supplies to the long term facility to assess and repair the issue and/or to resupply the missing pharmaceuticals 330. In some embodiments, if there is not a second dispensing machine off-site in the vicinity of the long term facility or the second dispensing machine off-site in the vicinity of the long term facility does not comprise the required pharmaceuticals (Flowchart continues following the letter L to FIG. 16), the server assesses if there is a pharmacy (or other relevant HMO) in the vicinity of the long term facility 332. In some embodiments, if the answer is yes and there is a pharmacy nearby, the server assesses if the pharmacy has a dispensing machine from the pharmaceutical dispensing system 334. In some embodiments, if the answer is yes and the pharmacy has a dispensing machine, then the server changes the primary dispensing machine to the machine as the primary dispensing machine of the long term facility 336, and dispatches a technician and/or dispatches pharmaceuticals supplies to the long term facility to assess and repair the issue and/or to resupply the missing pharmaceuticals 338. In some embodiments, if the answer is no and the pharmacy does not have a dispensing machine, then the server activates the pharmacy by requesting the necessary pharmaceuticals, which will be provided as soon as possible to the long term facility 340, and dispatches a technician to the long term facility to assess and repair the issue 338.

In some embodiments, the answer to the inquiry regarding the availability of a pharmacy nearby is no. In some embodiments, at this point (Flowchart continues following the letter M to FIG. 17), the server assesses if there is a second dispensing machine in an off-site 342 location distant from the long term facility. In some embodiments, if the answer is yes, then the server assesses if the second dispensing machine in the off-site, which is far from the long term facility, comprises the necessary pharmaceuticals for the correct dispensing in the long term facility 344. In some embodiments, if the second dispensing machine in the off-site far from the long term facility comprises the necessary pharmaceuticals, the system changes the primary dispensing machine to the second dispensing machine in the far off-site as the primary dispensing machine of the long term facility 346, and dispatches a technician and/or dispatches pharmaceuticals supplies to the long term facility to assess and repair the issue and/or to resupply the missing pharmaceuticals 348. In some embodiments, if there is not a second dispensing machine in an off-site location distant from the long term facility or the second dispensing machine in the off-site far from the long term facility does not comprise the required pharmaceuticals (Flowchart continues following the letter N to FIG. 18), the server assesses if there is a storage unit in the vicinity of the long term facility 350. In some embodiments, if the answer is yes and there is a storage unit nearby, the server assesses if the storage unit has a dispensing machine from the pharmaceutical dispensing system 352. In some embodiments, if the answer is yes and the storage unit has a dispensing machine, then the server changes the primary dispensing machine to the dispensing machine of the storage unit as the primary dispensing machine of the long term facility 354, dispatches a technician and/or dispatches pharmaceuticals supplies to the long term facility to assess and repair the issue and/or to resupply the missing pharmaceuticals 356. In some embodiments, if the answer is no and the storage unit does not have a dispensing machine, then the server activates the storage unit by requesting the necessary pharmaceuticals, which will be provided as soon as possible to the long term facility 358, and dispatches a technician and/or dispatches pharmaceuticals supplies to the long term facility to assess and repair the issue and/or to resupply the missing pharmaceuticals 356. In some embodiments, if there is no storage unit in the near vicinity of the long term facility, the server contacts a human supervisor 360 to notify him of the issue.

Returning to FIG. 13, if the issue is a consumable issue 312, then (Flowchart continues following the letter I to FIG. 19), then the system assesses if the consumable is replaceable by the personnel in-site (i.e. nurse) 362. In some embodiments, if the answer is yes, the system notifies the personnel 364 that a consumable needs to be replaced and/or refilled, and then system dispatches consumables and/or a technician 366. In some embodiments, if the consumable is not replaceable by the personnel, then the system assesses if there is a second dispensing machine on-site 368. In some embodiments, if there is, the system assesses if the second dispensing machine comprises the necessary pharmaceuticals for the correct dispensing in the long term facility 370. In some embodiments, if the second dispensing machine comprises the necessary pharmaceuticals, the system changes the primary dispensing machine to the back-up dispensing machine 372, and dispatches consumables and/or a technician 374. In some embodiments, if the second dispensing machine does not comprise the necessary pharmaceuticals and/or if there is not a second dispensing machine on-site, then (Flowchart continues following the letter K back to FIG. 15) the server assesses if there is a second dispensing machine off-site 324 in the vicinity of the long term facility. The next actions following this assessment are the same as disclosed above, with the difference that consumables are dispatched instead of pharmaceuticals.

Returning to FIG. 13, if the issue is a security issue 310, then (Flowchart continues following the letter H to FIG. 20), then the system commences two independent actions. In some embodiments, the system activates the locking mechanism of the dispensing machine 376 and assesses if there are sensitive drugs in the dispensing machine 378. In some embodiments, if there are sensitive drugs, then the system contacts the authorities (i.e. police) 380 and dispatches relevant personnel (i.e. technician, supervisor) 382. In some embodiments, the second action is to assess if there is a second dispensing machine on-site 384. In some embodiments, there is, the system assesses if the second dispensing machine comprises the necessary pharmaceuticals for the correct dispensing in the long term facility 386. In some embodiments, if the second dispensing machine comprises the necessary pharmaceuticals, the system changes the primary dispensing machine to the back-up dispensing machine 388. In some embodiments, if the second dispensing machine does not comprise the necessary pharmaceuticals and/or if there is not a second dispensing machine on-site, then (Flowchart continues following the letter K back to FIG. 15) the server assesses if there is a second dispensing machine off-site 324 in the vicinity of the long term facility. The next actions following this assessment are the same as disclosed above.

Exemplary Pharmaceutical Dispensing Storage system

In some embodiments, a plurality of storage units are part of the pharmaceutical dispensing system. In some embodiments, the storage units comprise a plurality of pharmaceuticals according to the requirements of the long term facilities having pharmaceutical dispensing machines, which are located in the vicinity of the storage unit. In some embodiments, the server monitors the requirements of the different long term facilities and distributes accordingly the pharmaceuticals in the storage units.

In some embodiments, the server comprises a dedicated software that monitors the requirements of a specific area, collects the information in dedicated databases and performs analysis on the information. In some embodiments, based on the information, the server is capable to anticipate the needs of different zones and activate the timely delivery of supplies according to their expected needs. In some embodiments, the information includes, for example, the pharmaceuticals shelf life, the pharmaceuticals costs (for example, ordering pharmaceuticals having similar active ingredients but cost less), the expected time of supply from the pharmaceuticals suppliers, the type of pharmaceuticals needed in the region, the time of year (for example, expecting more cases of flu during the winter), pharmaceuticals that need special handling requirements (e.g. refrigeration, exposure to light), pharmaceuticals that need to be under lock, the form that the pharmaceutical is provided (i.e. liquid, powder, pill, IV).

In some embodiments, a single storage unit can supply pharmaceuticals to a variety of long term facilities in the same region. In some embodiments, a single storage unit can supply pharmaceuticals to adjacent regions, each region comprising a variety of long term facilities.

In some embodiments, the software is adapted to monitor and match the National Drug Code (NDC) of the pharmaceuticals. In some embodiments, monitoring and matching of the pharmaceuticals by their NDC is performed at any time that any pharmaceutical is moved, for example, when being loaded into envelopes and/or when being loaded into dispensing machines. In some embodiments, monitoring and matching of the pharmaceuticals by their NDC may reduce incidents where an incorrect pharmaceutical is being loaded and/or dispensed.

In some embodiments, the system comprises a dedicated algorithm responsible for the storage organization of the pharmaceuticals. In some embodiments, the storage organization is dictated by a plurality of parameters. Exemplary parameters are:

Required pharmaceuticals for the current population in the facilities, and between them: common prescribed pharmaceuticals, pharmaceuticals that need to be dispensed on a regular basis, predicted and commonly used pharmaceuticals that are not yet prescribed to specific tenants but likely to be required.

Life expectancy of the pharmaceuticals, for example, not to keep pharmaceuticals that are likely to expire unless consumed regularly by the current tenants.

Storage pharmaceuticals between the different storage devices (in case more than one dispensing machine is in the site) based on, for example, location of use, frequency of use, type of drug (i.e. bulk, liquid, powder), Storage pharmaceuticals based on multiple facilities, for example, for rare drugs use facility to store rare drugs for another facility in close proximity.

Consolidate and storage same drug from different makers.

Storage pharmaceuticals based on costs, for example, batch production vs one at a time, expiration time, special storage requirements (e.g. refrigeration), consistency of drugs (e.g. liquid, powder, pills).

Storage pharmaceuticals based on costs of buying the pharmaceuticals from the providers (e.g. same drug can be bought at different prices at different locations).

Storage pharmaceuticals based on the level of automation of the storage facility, for example, manual storage lockers, fully computerized storage facility.

In the past, storage of pharmaceuticals was directly decided by the actual location of the users, for example, a long term facility would store the required pharmaceuticals in-house since the users are located in the long term facility. Therefore, it was expected that the storage of pharmaceuticals would be, for example, on the same place as the users. Different cases might provide different expected storage locations. In some embodiments, the actual storage location of the pharmaceuticals is different from the expected storage location of the pharmaceuticals. In some embodiments, the storage placement of the pharmaceuticals is not the same place as the users. Referring now to FIG. 21, showing a schematic representation of a methodology of organizing the storage of pharmaceuticals in a pharmaceutical dispensing system. In some embodiments, the system comprises the information regarding an expected location for pharmaceutical storage 390. In some embodiments, the system analyzes the data regarding each pharmaceutical according to defined parameters 392. In some embodiments, the actual storage placement of the pharmaceuticals is different from the expected storage placement 394. In some embodiments, the system does not require the information regarding an expected location for pharmaceutical storage 390 for providing a storage placement for pharmaceuticals.

Exemplary Pharmaceutical Dispensing System—user Tracking System

One of the downsides of the prior art system is that the system is not updated with the location of the patients in real-time. For example, a patient in a hospital is required to take a medicine at a certain time. So it happens, that at that same time the patient was transferred to another department inside the hospital, for example physiotherapy. The nurse, or any other personnel responsible for giving the medicine to the patient, is now required to look for the patient, find him and ensure that the patient will get the medicine on time. This causes a waste of time and resources. A worse scenario, is the possibility that the patient might get a double dose, one at the physiotherapy department and another once he is back. This might endanger the health of the patient. Another example, a patient in a long term facility decides to spend the holidays with his family. If the system is not updated with the location of the patient, the dispensing machine will keep dispensing his medicine even if he is not located in the long term facility. This, again, causes a waste of resources.

In some embodiments, the pharmaceutical dispensing system comprises a personalized tracking system, adapted to include real-time information on the location of each patient.

In some embodiments, the tracking system comprises a daily schedule for each patient. In some embodiments, the schedule is updated by the user and/or the medical personnel of the facility. In some embodiments, the schedule comprises all the information regarding all the hours of the day, all the days of the year, and more.

In some embodiments, the server activates dedicated delivery services (e.g. special delivery services like UPS® or FEDEX®, a nurse, a pharmacy) using the information from the tracking system in order to dispense pharmaceuticals at the real-time location of the patient. In some embodiments, the patient can access a local pharmacy where the pharmaceuticals will be waiting for him.

In some embodiments, the location of the patient is updated manually by the long term facility personnel. In some embodiments, the location of the patient is tracked using an electronic tag, which is in communication with the system and provides real-time updates on the location of the patient. In some embodiments, the location of the patient is tracked using the personal electronic devices of the patient, for example, cellphone, tablet, smartwatch. In some embodiments, the location of the patient is tracked using a dedicated device provided to the patient.

Referring now to FIG. 22, showing a schematic flowchart of a tracking method performed by an exemplary server of the pharmaceutical dispensing system. In some embodiments, the system inquiries if the patient will be at his regular location 396. Optionally, the system inquiries if the patient is currently at his regular location. If the answer is yes, then the system continues with the dispensing regularly 398. If the answer is no, them the system inquiries if the patient is at other location inside the facility 400. If the answer is yes, then the system updates the location, as a temporary location of the patient in the facility 402. If the answer is no, then the system inquiries if the patient is at other facility 404. If the answer is yes, then the system updates the address of the other facility as temporary location, and transfers the drug prescriptions to the other facility 406. If the answer is no, then the system inquiries if the patient is at other address but not in a facility 408. If the answer is yes, then a personal drug package is prepared and sent to the new temporary address 410. If the answer is no, then the system evaluates the patient status 412, for example, deceased, not sick anymore, permanently moved to another facility.

Exemplary Connection and or Interface between the Electronic Medical Record of the Facility and Management Software Referring now to FIG. 23 showing a schematic representation of the connection and/or interface between the electronic medical record of the facility and the plurality of management softwares, according to some embodiments of the represent invention.

In some embodiments, each region (or facility, or plurality of facilities in a specified area) comprises a regional server 500 (also called regional environment) adapted to hold the relevant database functionalities and relevant services from the management system software 502 (DxAgent). In some embodiments, this server is connected to the outside real live residents 504 data coming from the framework 506 (electronic medical record) of the facilities. In some embodiments, there can be a finite number N of region servers/enviroments 508.

In some embodiments, the plurality of region servers/enviroments are connected to a root server/enviroment 510, which contains major data and management services for all the APS 512 (Advances Pharmaceutical Solutions—e.g. large dispensing machine 100, small dispensing machine 101, bulk storage cabinet 103, a refrigerator 105, a nursing cart 107) units located in the same area. In some embodiments, where there is a server-client infrastructure the live data is kept on the server with duplication on the local unit in order to allow continuous activity in case of disconnection between the single machines and the servers. In some embodiments, the APS units comprise several APS-mini 514, which can be secondary machines that are directly connected (master-slave mode) in order to provide dispensing services to the same population. In some embodiments, the root server/enviroment 510 is connected and updates the warehouse systems with the necessary data 516.

Optional Components of an Exemplary System

It should be understood that the devices (e.g. dispensing machines) and methods disclosed thereof, include the use of known and disclosed methods performed by the server, said server having a dedicated database including the necessary information required for the correct functioning of the pharmaceutical dispensing system; and performed by the warehouse, said warehouse comprising the necessary pharmaceuticals required by the dispensing machines. While not explicitly mentioned in each embodiment, it should be understood that they optionally include the servers and the warehouses as integral parts of the pharmaceutical dispensing system, unless mentioned otherwise.

As used herein with reference to quantity or value, the term "about" means "within ±20% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a unit" or "at least one unit" may include a plurality of units, including sub-units thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of providing a pharmaceutical dispensing service to at least one user in at least one facility, comprising:
   a. providing at least one first pharmaceutical storage and dispensing machine to said at least one first facility, said at least one first pharmaceutical storage and dispensing machine that stores a plurality of different pharmaceuticals, retrieves an individual pharmaceutical from said plurality of different pharmaceuticals, loads said individual pharmaceutical into one of a plurality of disposable individual patient dosing packages, packages said individual pharmaceutical, and dispenses said individual patient dosing package into a separate and removable container associated with said machine for use by authorized personnel located at said facility, said dispense is according to schedules of said patients;
   b. providing a pharmacy group management computer being positioned remote from said at least one first facility and that manages and controls said at least one first pharmaceutical storage and dispensing machine defining a facility pharmacy management server;
   c. running a self-diagnostic program in said at least one first pharmaceutical storage and dispensing machine for revealing a possible problem with said dispensing of said plurality of different pharmaceuticals;
   d. when said possible problem with said dispensing is revealed, then providing at least one supplemental supplier of individual pharmaceuticals loaded and packed in disposable individual patient dosing packages;

wherein said method further comprises instructions for:
   i. tracking expected needs by means of pharmaceutical prescriptions related to said at least one user stored in said pharmacy group management computer;
   ii. tracking a level of urgency that said at least one user requires said dispensing of pharmaceuticals, said urgency defined as potentially endanger the health of said at least one user due to non-dispensing of pharmaceuticals; and
   iii. tracking delivery of pharmaceuticals to said at least one pharmaceutical storage and dispensing machine; and said method further comprising instructions for selecting said at least one supplemental supplier of individual pharmaceuticals loaded and packed in disposable individual patient dosing packages to ensure dispensing of pharmaceuticals to said at least one user according to a predetermined schedule.

2. The method of claim 1, further comprising providing at least one second pharmaceutical storage and dispensing machine as supplemental supplier of pharmaceuticals.

3. The method of claim 2, wherein said providing at least one second pharmaceutical storage and dispensing machine further comprises allocating said at least one second pharmaceutical storage and dispensing machine at the same facility as said at least one first pharmaceutical storage and dispensing machine.

4. The method of claim 2, wherein said providing at least one second pharmaceutical storage and dispensing machine further comprises allocating said at least one second pharmaceutical storage and dispensing machine at a second facility; said second facility is located at a relative physical distance from about 0 kilometers to about 1000 kilometers from said at least one first facility or said second facility is located at a relative period of time required to travel between said second facility and said at least one first facility of from about 0 minutes to about 20 hours.

5. The method of claim 2, wherein said providing at least one second pharmaceutical storage and dispensing machine further comprises allocating said at least one second pharmaceutical storage and dispensing machine at a third facility; said third facility is located at a relative physical distance is of about 1000 kilometers or more or at a relative period of time required to travel between said second facility and said at least one first facility of about 24 hours or more.

6. The method of claim 1, further comprising providing communication with at least one pharmacy as supplemental supplier of pharmaceuticals.

7. The method of claim 6, wherein said pharmacy comprises a pharmaceutical storage and dispensing machine.

8. The method of claim 1, further comprising providing communication with at least one storage unit as supplemental supplier of pharmaceuticals.

9. The method of claim 1, wherein information regarding said predetermined schedule is located in said pharmacy group management computer.

10. The method of claim 1, wherein said selecting said at least one supplemental supplier of pharmaceuticals comprises evaluating at least one parameter related to said supplemental supplier for said selecting of said at least one supplemental supplier of pharmaceuticals.

11. The method of claim 10, wherein said at least one parameter is selected from the group consisting of:
   a. a distance between said at least one facility and said at least one supplemental supplier of pharmaceuticals;
   b. a period of time required to move between said at least one facility and said at least one supplemental supplier of pharmaceuticals;
   c. a nature of the problem that caused said at least one first pharmaceutical storage and dispensing machine to not being able to provide said dispensing of pharmaceuticals; and
   d. a level of urgency that said at least one user requires said dispensing of pharmaceuticals.

12. The method of claim 10, wherein said at least one parameter is a distance between said at least one facility and said at least one supplemental supplier of pharmaceuticals.

13. The method of claim 1, further comprising providing said at least one first pharmaceutical storage and dispensing machine with self-diagnostic capabilities adapted to perform self-diagnostic actions related to software, hardware and inventory of said at least one first pharmaceutical storage and dispensing machine.

14. A system of pharmaceutical dispensing for at least one first facility, comprising:
   a. a data processing and management computer including a first memory to store data therein to manage and control at least one pharmaceutical storage and dispensing machine positioned remote therefrom and to thereby define a facility pharmacy group management server;
   b. a facility pharmacy management software stored in said first memory of said facility pharmacy group management server to manage pharmaceutical operations in said at least one facility, to process distribution of pharmaceuticals stored in said at least one pharmaceutical storage and dispensing machine during preselected dispensing time periods;

c. a communications network in communication with said facility pharmacy group management server;

d. at least one pharmaceutical storage and dispensing machine positioned in said at least one facility remote from said facility pharmacy group management server, in communication with said facility pharmacy group management server through said communication network, that stores a plurality of different pharmaceuticals therein, and retrieves an individual pharmaceutical from said plurality of pharmaceuticals stored in said pharmaceutical storage and dispensing machine, loads said individual pharmaceutical into one of a plurality of disposable individual patient dosing packages, packages said individual pharmaceutical, and dispenses said loaded and packaged one of said plurality of individual patient dosing packages into a separate and removable container associated with said machine for use by authorized personnel located at said facility, wherein said at least one pharmaceutical storage and dispensing machine performs said dispensing under computer control to match dispensing schedules of a plurality of patients;

wherein said system further comprises at least one supplemental supplier of said plurality of pharmaceuticals adapted to dispense said individual pharmaceuticals loaded and packed in disposable individual patient dosing packages to the users at said preselected dispensing time periods;

said facility pharmacy management software comprises instructions for running a self-diagnostic program in said at least one first pharmaceutical storage and dispensing machine for tracking a dispensing ability of said at least one pharmaceutical storage and dispensing machine and for revealing a possible problem with said dispensing of said plurality of different pharmaceuticals; determining expected needs by means of pharmaceutical prescriptions related to said plurality of patients stored in said pharmacy group management server; determining a level of urgency that said plurality of patients require said dispensing of pharmaceuticals, said urgency defined as potentially endanger the health of said plurality of patients due to non-dispensing of pharmaceuticals; and instructions for selecting said at least one supplemental supplier of pharmaceuticals in response to said determined expected needs and dispensing ability.

15. The system of claim 14, wherein said at least one supplemental supplier is a second pharmaceutical storage and dispensing machine located at the same facility.

16. The system of claim 14, wherein said at least one supplemental supplier is a second pharmaceutical storage and dispensing machine located at a second facility; said second facility is located at a relative physical distance from about 0 kilometers to about 1000 kilometers from said at least one first facility or said second facility is located at a relative period of time required to travel between said second facility and said at least one first facility of from about 0 minutes to about 20 hours.

17. The system of claim 14, wherein said at least one supplemental supplier is a second pharmaceutical storage and dispensing machine located at a second facility; said second facility is located at a relative physical distance is of about 1000 kilometers or more or at a relative period of time required to travel between said second facility and said at least one first facility of about 24 hours or more.

18. The system of claim 14, wherein said at least one supplemental supplier is a pharmacy located near said facility.

19. The system of claim 14, wherein said at least one supplemental supplier is a storage unit.

20. The system of claim 14, wherein said instructions comprise evaluating at least one parameter related to at least one supplemental supplier said for said selecting of said at least one supplemental supplier of pharmaceuticals.

21. The system of claim 20, wherein said at least one parameter is selected from the group consisting of:
 a. a physical distance between said at least one facility and said at least one supplemental supplier of pharmaceuticals;
 b. a period of time required to move between said at least one facility and said at least one supplemental supplier of pharmaceuticals;
 c. a nature of the problem that caused said at least one first pharmaceutical storage and dispensing machine to not being able to provide said dispensing of pharmaceuticals; and
 d. a level of urgency that said at least one user requires said dispensing of pharmaceuticals.

22. The system of claim 20, wherein said at least one parameter is a physical distance between said at least one facility and said at least one supplemental supplier of pharmaceuticals.

23. The system of claim 14, further comprising self-diagnostic capabilities adapted to perform self-diagnostic actions related to software, hardware and inventory of said system.

* * * * *